(12) United States Patent
Lopez et al.

(10) Patent No.: US 12,083,288 B2
(45) Date of Patent: Sep. 10, 2024

(54) ONE-MOTION HANDLE FOR STEERABLE CATHETER

(71) Applicant: Biosense Webster (Israel) Ltd., Yokneam (IL)

(72) Inventors: Simon Lopez, Irvina, CA (US); Cesar Fuentes-Ortega, Pasadena, CA (US); Pieter Emmelius Van Niekerk, Rancho Santa Margarita, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 269 days.

(21) Appl. No.: 17/487,226

(22) Filed: Sep. 28, 2021

(65) Prior Publication Data

US 2022/0168545 A1 Jun. 2, 2022

Related U.S. Application Data

(60) Provisional application No. 63/120,493, filed on Dec. 2, 2020.

(51) Int. Cl.
*A61M 25/00* (2006.01)
*A61M 25/01* (2006.01)

(52) U.S. Cl.
CPC .... *A61M 25/0136* (2013.01); *A61M 25/0021* (2013.01); *A61M 25/0147* (2013.01); *A61M 2025/0024* (2013.01)

(58) Field of Classification Search
CPC .......... A61M 25/0136; A61M 25/0021; A61M 25/0147; A61M 2025/0024;
(Continued)

(56) References Cited

U.S. PATENT DOCUMENTS 5,364,352 A * 11/1994 Cimino ............. A61M 25/0136
604/524
5,885,278 A * 3/1999 Fleischman ........ A61B 18/1492
606/41

(Continued)

FOREIGN PATENT DOCUMENTS

CN 103565518 B 9/2015

OTHER PUBLICATIONS

International Search Report & Written Opinion dated Feb. 28, 2022, from corresponding International Application No. PCT/IB2021/060790.

(Continued)

*Primary Examiner* — Nathan R Price
*Assistant Examiner* — Haden Matthew Ritchie
(74) *Attorney, Agent, or Firm* — Troutman Pepper Hamilton Sanders LLP

(57) ABSTRACT

A control handle for a steerable catheter allows for precise manipulation of the distal catheter tip in a target organ or vessel using only one hand. The control handle can have a single articulating knob capable of both linear translation along and rotation about the axis of the handle. These functions of the articulating knob actuate both the expansion and retraction of an expandable member, as well as bi-directional deflection of the distal catheter tip. The articulating knob functions with consistency regardless of the orientation of the handle, with ergonomic movements allowing the user to comfortably keep their attention on the procedure's monitoring equipment. These improvements can lead to safe and more rapid procedure times for procedures such as diagnostics and cardiac ablation.

16 Claims, 21 Drawing Sheets

(58) Field of Classification Search
CPC .. A61B 2018/0022; A61B 2018/00946; A61B 2018/00952; A61B 18/1492
See application file for complete search history.

(56) References Cited

U.S. PATENT DOCUMENTS

| | | | |
|---|---|---|---|
| 5,944,690 A | 8/1999 | Falwall et al. | |
| 6,024,740 A | 2/2000 | Lesh et al. | |
| 6,012,457 A | 7/2000 | Lesh | |
| 9,326,813 B2 | 5/2016 | Pike, Jr. et al. | |
| 9,468,495 B2 * | 10/2016 | Kunis | A61B 18/1815 |
| 2012/0271301 A1 | 10/2012 | Fischell et al. | |
| 2014/0018732 A1 * | 1/2014 | Bagaoisan | A61M 25/0136 |
| | | | 604/95.04 |
| 2014/0276397 A1 * | 9/2014 | Terwey | A61M 25/0136 |
| | | | 604/95.04 |
| 2016/0175041 A1 * | 6/2016 | Govari | A61B 18/1492 |
| | | | 606/41 |
| 2016/0331932 A1 | 11/2016 | Davies et al. | |
| 2018/0154114 A1 * | 6/2018 | Tang | A61M 39/06 |
| 2019/0083751 A1 | 3/2019 | Buesseler | |
| 2021/0283373 A1 * | 9/2021 | Porter | A61M 25/0147 |

OTHER PUBLICATIONS

International Preliminary Report on Patentability dated May 30, 2023, from corresponding International Application No. PCT/IB2021/060790.

* cited by examiner

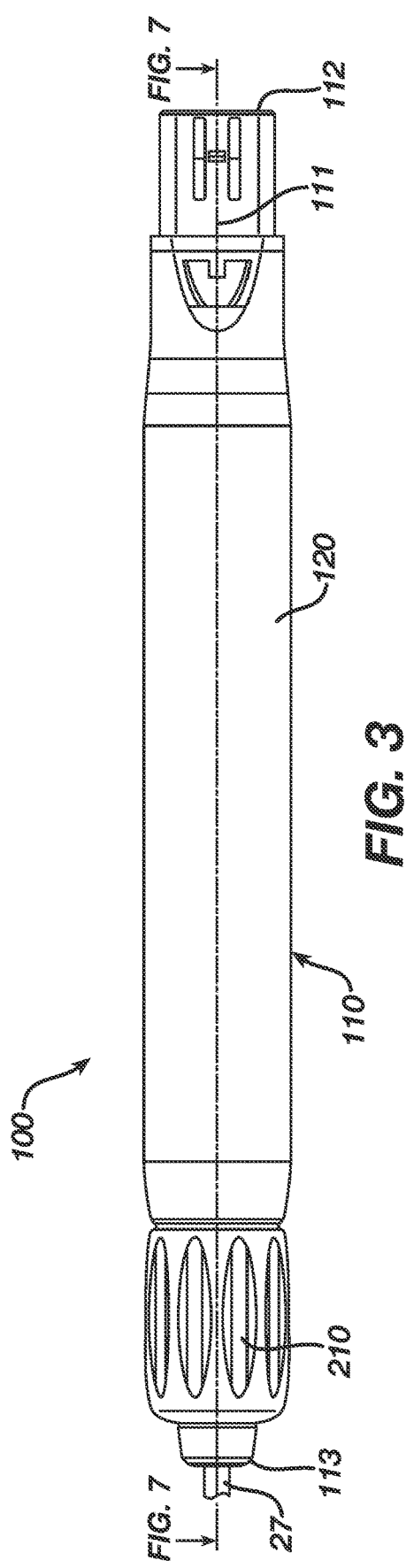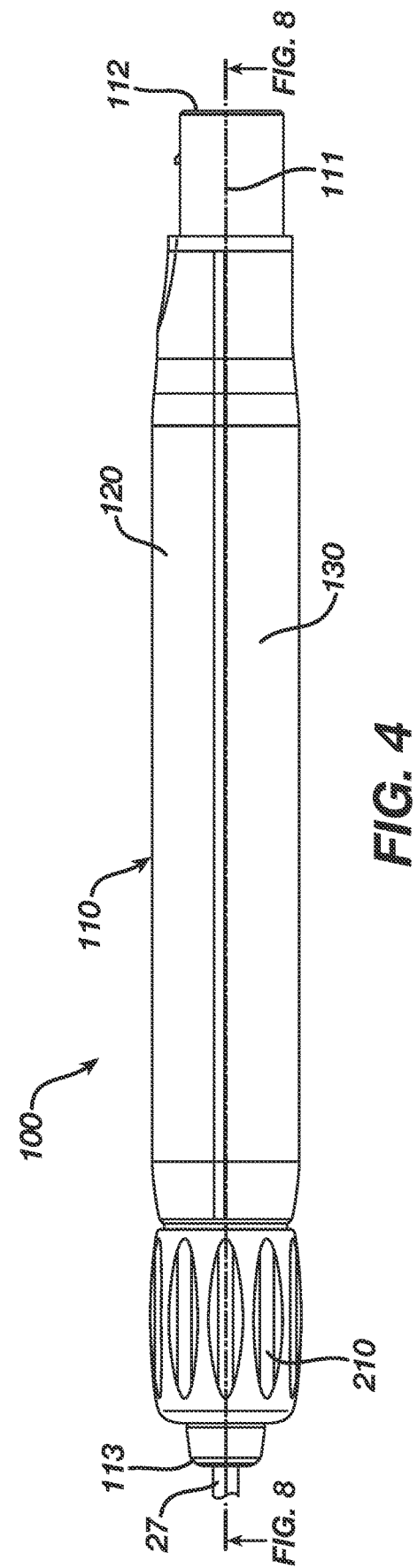

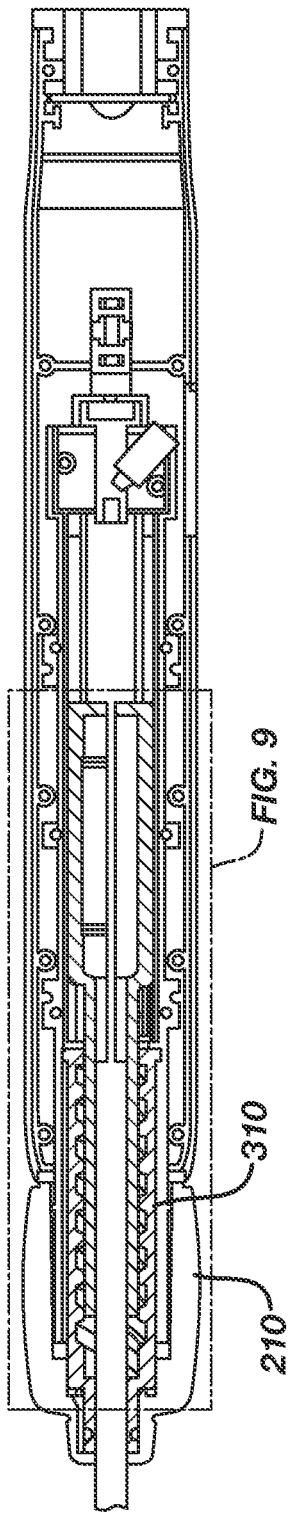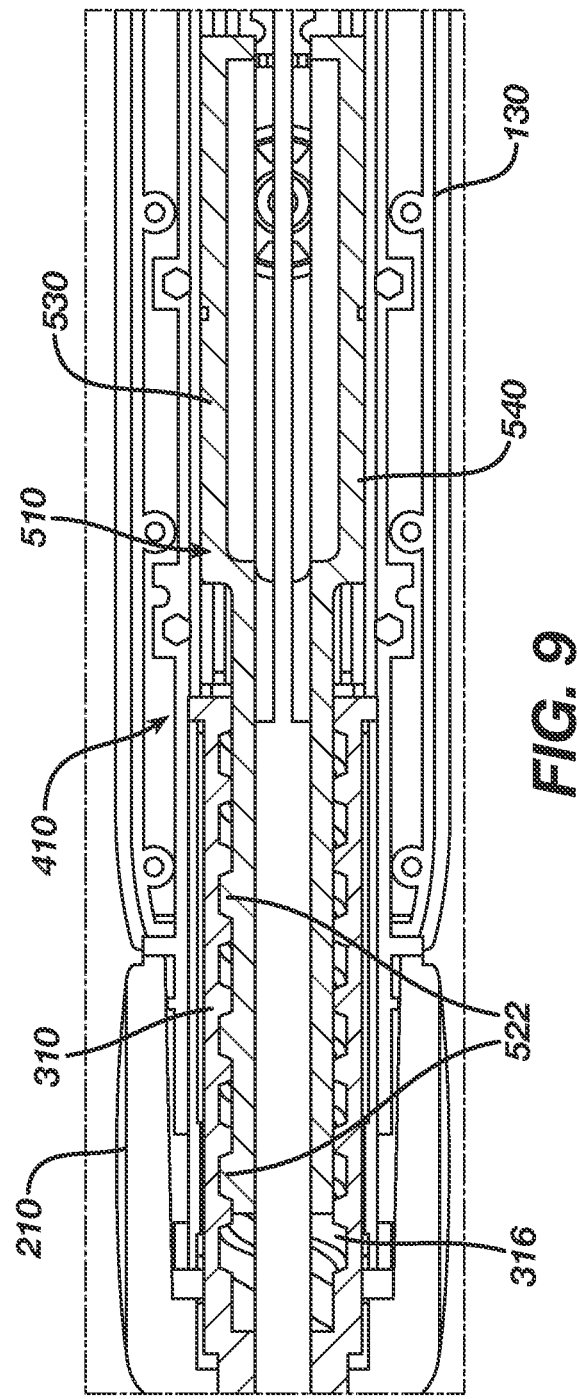

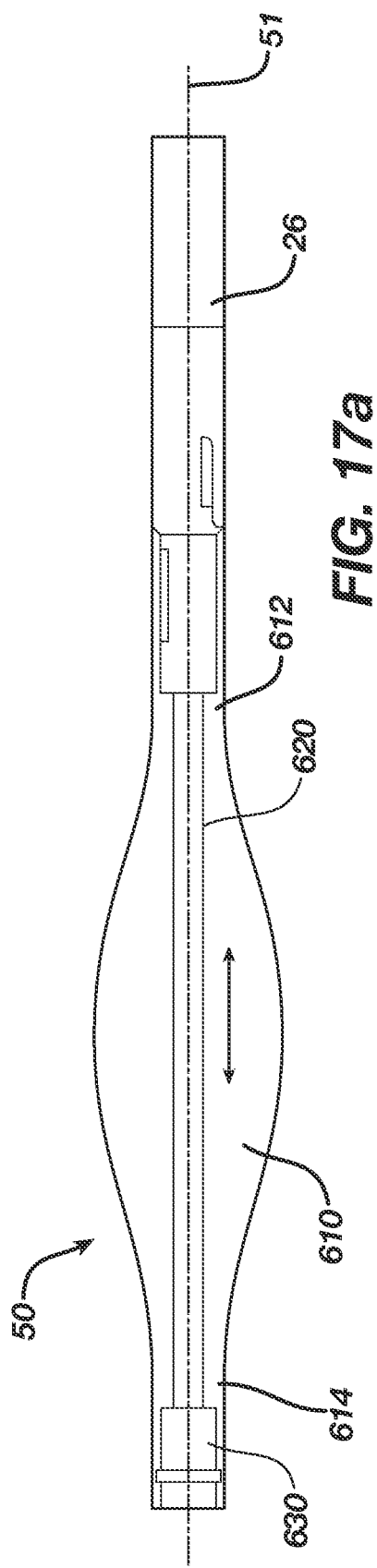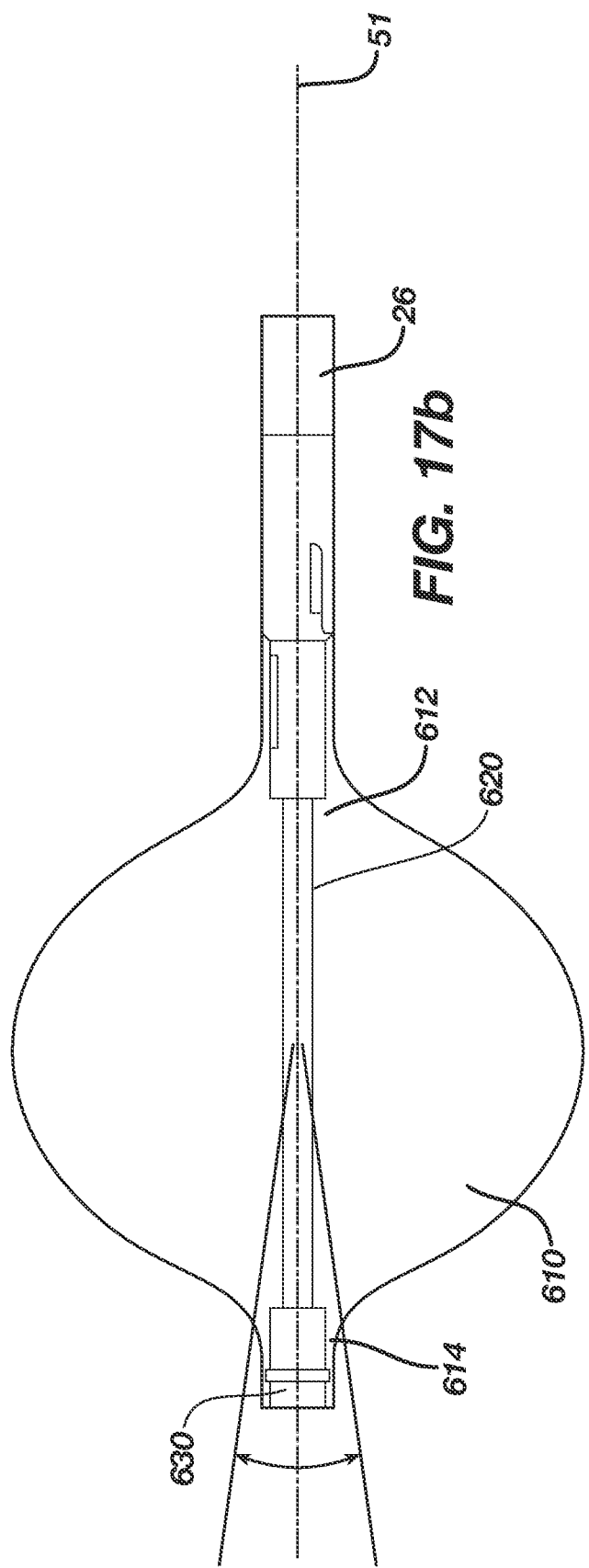

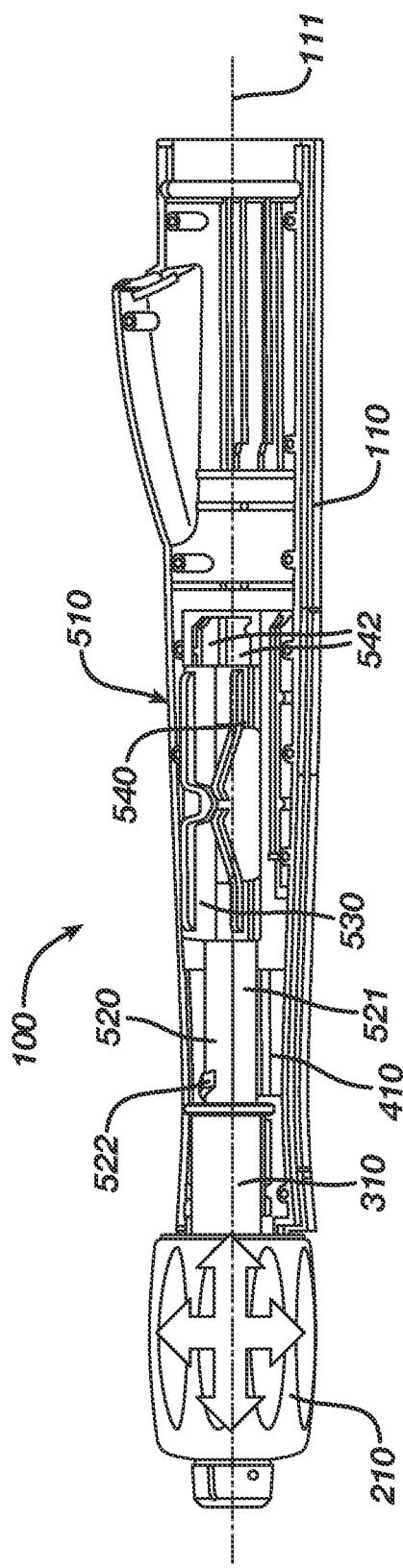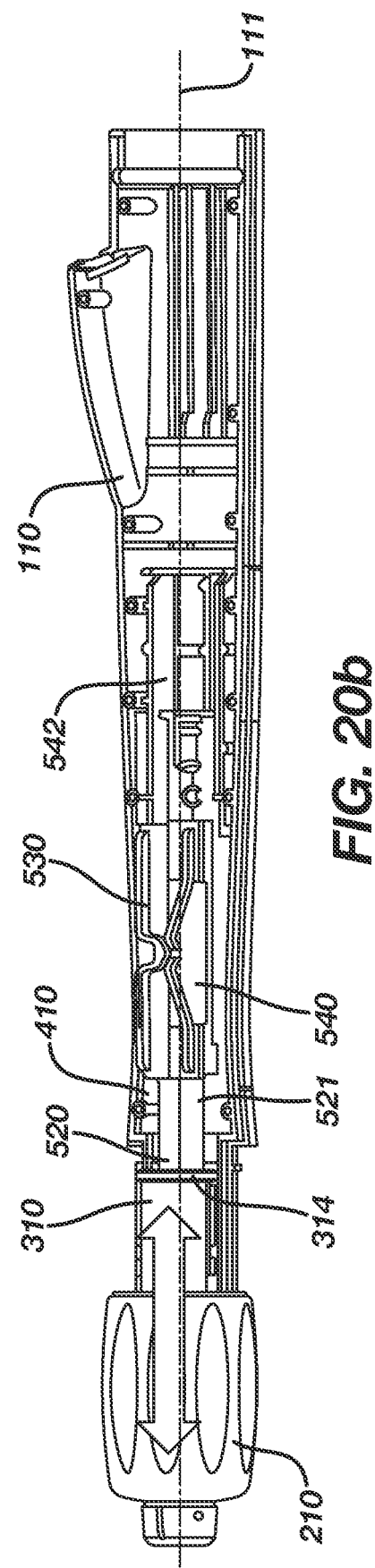

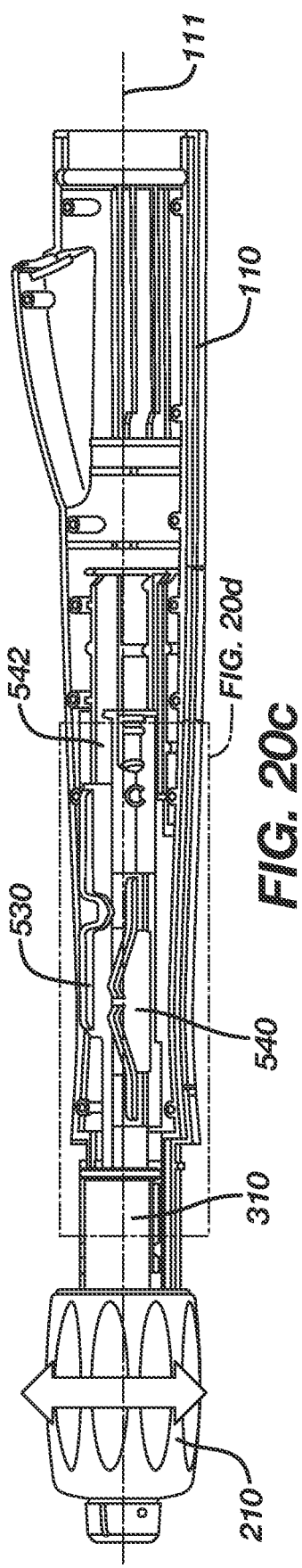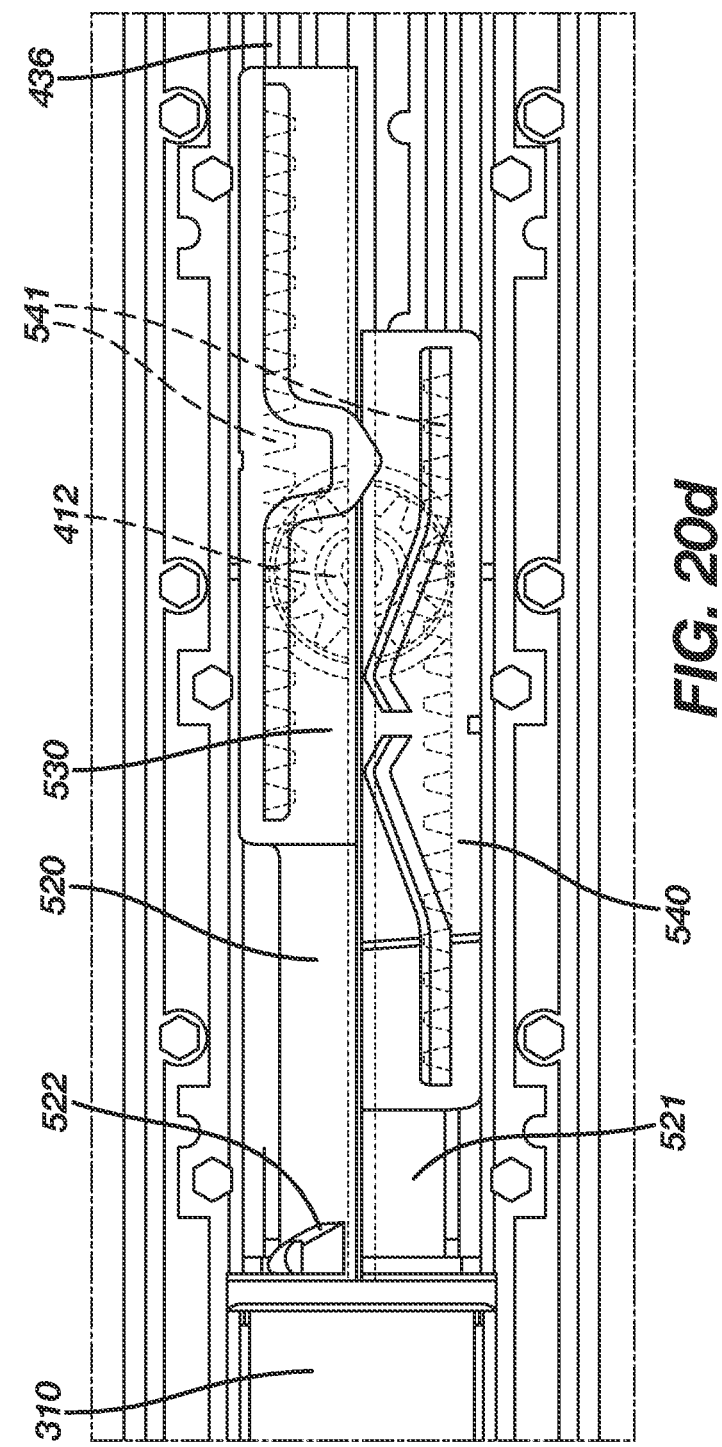

ONE-MOTION HANDLE FOR STEERABLE CATHETER

CROSS-REFERENCE TO RELATED APPLICATION

The present application claims the benefit of priority under the Paris Convention and 35 USC § 119 of U.S. Provisional Patent Application No. 63/120,493, filed on Dec. 2, 2020 and incorporated herein by reference in its entirety as if set forth in full into this application.

FIELD OF INVENTION

The present invention generally relates to a control handle for intravascular catheter systems, and more particularly, the present disclosure to relates to improved handles for steerable catheters which can be operated with one hand.

BACKGROUND

Abnormal or erratic electrical signals in regions of cardiac tissue can disrupt normal heart rhythm. Cases of heart arrhythmia are the result of irregular heartbeat cycles in which these electrical signals are not coordinated properly. Such conditions, which include Paroxysmal Atrial Fibrillation (PAF), are often treated either by either disrupting the origins of the signals, or through severing the conductive pathway for the signals through the pulmonary veins.

Many procedures require the use of multifunction catheters with tip mechanisms capable of being steered or expanded and retracted. Many such procedures, like diagnostics mapping and ablation, require a high level of precision. Ablation techniques are commonly used for ceasing or modifying the propagation of unwanted electrical signals from one portion of the heart to another. This process involves applying energy to the tissue from electrodes which destroys unwanted electrical pathways through the formation of non-conductive lesions. The applied energy can be Radiofrequency (RF), cryogenic, irreversible electroporation (IRE), or other similar techniques. Successful patient outcomes are often reliant on precisely-targeted isolation of the pulmonary veins in the subject's left atrium to eliminate the symptoms. The deliverability specialized catheters, and the deployment of precision ablation assemblies to an expanded configuration after delivery, creates continual challenges to improve the control elements for these systems.

Typical catheter systems usually involve an elongated flexible catheter shaft extending from a proximal luer or control handle containing an actuation mechanism or mechanisms. Some of these catheters are capable of delivering steerable tips to cardiac or other tissues of the body for the purpose of ablation, diagnostics, or other functions to aid in treatment. The use of a radially-expanding device with RF electrodes for creating circumferential lesions at or near the ostia of the pulmonary veins to treat atrial arrhythmia are disclosed in U.S. Pat. Nos. 6,012,457 and 6,024,740, both to Lesh. In addition, U.S. Pat. Publication No. 2016/0175041 to Govari et al., which is commonly assigned herewith and herein incorporated by reference, utilizes a catheter with an expandable balloon having an electrode assembly disposed about its exterior such that atraumatic contact with the vein ostia can produce consistent circumferential lesions with circumscribe the veins.

However, intravascular procedures using steerable catheters are still encumbered by the difficulties experienced by the user in attempting to maneuver the catheter tip to precise tissue locations. Existing catheters, even those with steerability and deflection control, often have limited maneuverability capabilities. This is especially true of procedures where particularly fine movement control is required. Further, existing designs are often capable of deflection along a single plane, meaning the user must rotate the entire device to access three-dimensional locations not parallel to the deflection plane. This combination of factors can make many procedures, such as the alignment of ablation electrodes, an arduous and time-consuming exercise. Uneven or incomplete ablation could lead to embolization of debris or even treatment failure, while long fluoroscopy and procedure times can also result in complications.

In addition, attention to detail and the knowledge of exactly how specific equipment will respond to inputs is important for any successful operation. Control members or handles are important for catheter shaft maneuverability and steering, both to pass the aortic arch and in positioning for the ablation process. Often, there is a lever or rotating member on the handle to cause deflection to steer the tip. A slidable button or toggle mechanism can also be used. Precision and comfort of the handle are of importance, because if the catheter is turned, deflected, or rotated in the wrong direction serious injury to the patient can result. Similarly, a physician needing to repeatedly look away from his diagnostic tools to see where his hand is located and what part of the handle needs to be actuated can add considerable time to an operation procedure.

Examples of several different handle mechanisms for the control of catheters and catheters tips designed for electrophysiological mapping and/or ablation can be found in the art. U.S. Pat. No. 5,944,690 to Falwell et al. discloses a steerable catheter control design which utilizes a slider mechanism to manipulate control wires. However, depending on the position of the slider mechanism, the design can require awkward contortions of the hand to enable the thumb or another finger to further adjust the slider. A single slider can also lack the precision necessary for minute manipulation and adjustment of the catheter.

For ablation procedures, the geometry and size of the pulmonary veins often necessitates an ablation diameter that is considerably larger than the typical delivery catheter or sheath. As a result, many circumferential ablation devices are required to have both a flexible low-profile for delivery within an outer catheter but must deploy and expand to an enlarged configuration at the target site for accurate ablation or diagnostics. Actuating this expansion often requires additional functionality, fittings, or devices connected with or fed through the handle, complicating setup and requiring additional hands to operate. Similar capabilities are also required to contract the devices for retraction into the sheath or outer catheter upon completion of the procedure.

U.S. Pat. Publication No. 2019/0083751 to Buesseler discloses a plunger- or slider-type actuating mechanism for a medical device having a deflectable distal region. The device utilizes pinching of control wires as a means of securing or self-locking the mechanism in order to eliminate the need for a secondary locking feature and reduce operator fatigue. However, a plunger-type mechanism also has limited fine-control capability. Furthermore, these designs lack the capacity for further expansion or deployment functionality beyond manipulation of the tip.

A control handle for a steerable catheter disclosed in U.S. Pat. Publication No. 2016/0331932 to Davies et al. utilizes control wires articulated by one or more handle-mounted rotating knobs. Tensioning of the wires causes distal end deflections of the tip of the catheter. This design, however, can have multiple knobs at both the proximal and distal ends of the handle and may require multiple hands to manipulate in certain situations, while also lacking the capability of actuating further functions other than the steering of the tip.

Different physicians may also have different preferences in how they prefer to hold the handle during a procedure. Conventional handles or systems may have various control surfaces, which could be located proximally or distally on the handle, which requiring a physician to adapt significantly based on personal preferences and/or the dominance of a particular hand. As such these designs may not offer the necessary comfort for the user while manipulating and adjusting the handle.

There is therefore a need for improved devices, systems, and methods for control handles capable of fine steering control of the deflectable tip while also able to actuate further tip functions, such as the expansion and contraction of an expandable member. It is also highly preferable that the articulation of these functions can be performed with a single hand, such that the ergonomics of the handle do not impart fatigue on the operator.

SUMMARY

It is an object of the present invention to provide systems, devices, and methods to meet the above-stated needs. Generally, there is a specific need for precise control and actuation of catheters with mechanisms and devices capable of elongation and retraction and multidirectional deflection. Often, devices capable of consistent performance during procedures must be capable of activation between a collapsed delivery state and a deployed expanded state sized to deliver energy to the entire circumference of the ostium or to detect heart signals for diagnostics over a significant area. While often mentioned in the context of cardiac ablation or diagnostic procedures by way of example, many other potential applications for such a control handle can be envisioned, with any intravascular procedure requiring the remote actuation of an expandable member at a target site being a candidate.

A control handle for a catheter with a steerable tip can have an outer housing with a substantially tubular shape, a proximal end, and a distal end. An articulating knob for controlling functions of the catheter tip can be positioned approximate the distal end and configured to be rotatable about, and linearly displaceable along, a longitudinal axis of the outer housing of the handle. The handle housing and knob can be sized such that all the functions and movement of the knob can be comfortable performed with one hand, so the user will not need to look down to reference the respective position of handle components or use another hand for manipulation during a procedure. Movably disposed within the outer housing can be a drive housing longitudinally coupled to the articulating knob. The movement of the drive housing can actuate control members to initiate functions of the handle. The control members could include components such as control wires, sliding levers, or toggles.

In one example, the catheter can have electrodes at the steerable tip to be used for ablation of tissue in or around the heart to create enhanced lesions as a treatment to disrupt unwanted cardiac electrical signals. For example, one or more independently controlled electrodes can be disposed on the surface and equally spaced around the circumference of an inflatable balloon. In another example, electrodes can be situated on the outside of a structure which can be configured to expand when deployed from a delivery catheter at the target site. In this configuration, the catheter can have one or more luer fittings configured to receive fluid injection for irrigation of the ablation site and/or cooling of the tip electrodes.

In another example, the catheter can have a tip which can be triggered to expand in radial size or change shapes to perform, for example, electrophysiology mapping and imaging of healthy and unhealthy tissue of the heart. Such systems are often also capable of determining the speed and direction of cardiac signals.

The articulating knob can be configured to impart a first, a second, and a third linear displacement on the drive housing parallel to the longitudinal axis of the handle outer housing. In one case, a first linear displacement of the drive housing actuates a function of a first control member of the steerable tip, and a second linear displacement actuates a function of a second control member. The first linear displacement can occur when the knob is rotated clockwise about the longitudinal axis, and the second linear displacement can occur opposite the first linear displacement when the knob is rotated counterclockwise. These opposing displacements can tension control wires or cables coupled to the distal end of the catheter and cause the steerable tip to deflect angularly in opposing directions for directing fine motion of the tip at a target site in the vasculature.

The third linear displacement of the drive housing can occur when the articulating knob is translated a distal or proximal distance parallel to the longitudinal axis. The linear translation of the knob can be accomplished independently of any rotation imparted on the knob. This motion can be configured to change the radial size of an expandable member at the distal tip of the steerable catheter, such as the ablation balloon system for treating arrhythmia or a diagnostic tool configured to record cardiac signals from the tissues. This radial size can be actuated and controlled by an advancement mechanism coupled proximally to the drive housing and distally to the expandable element. A distal translation of the articulating knob could push the advancement mechanism distally to axially extend or elongate the expandable element, reducing its corresponding radial size. A similar proximal linear translation of the knob can pull the advancement mechanism to axially shorten and expand the expandable element. To accomplish this actuation, the advancement mechanism can be constructed of a tough but flexible organic material, such as polyimide tubing.

The advancement mechanism can be an elongate tubular member and have a hollow internal lumen. The lumen would allow the advancement mechanism to be used for the distal delivery of various auxiliary devices or treatments, such as guidewires, microcatheter-based systems, mapping catheters, or contrast media.

In a further example, the situation could be reversed to where linear translation of the articulating knob along the longitudinal axis actuates the steerable tip to deflect angularly in opposing directions for directing fine motion control, and a rotation of the articulating knob can be configured to control the radial size of the expandable element. The functions can thus be tailored to the ergonomic preferences of a particular user, or the ease of performing a specific procedure.

The articulating knob of the control handle can include a hub, a proximal end, and a distal opening through which the catheter body and any associated internals, such as the advancement mechanism and control members, can pass to the exterior of the handle. The inner diameter of the knob hub can have at least one keyway machined or formed into the surface. Rotatably coupled to the articulating knob can be a barrel nut. The barrel nut can include one or more keys, a thrust collar, and an internal drive spline. The keyway of the knob hub can transmit torque to the key of the barrel nut, which can be longitudinally and rotationally coupled to the drive housing though the thrust collar and the threads of the drive spline, respectively. The thrust collar can act as a mechanical stop to transmit linear displacement to the drive housing.

The drive housing can have a split piston carriage which can include a right deflection rack and a left deflection rack moveable with respect to each other in a controllable manner within the outer housing. The distal portions of the right and left deflection racks can form a drive bolt with external male threads configured to engage with the female drive spline threads of the barrel nut. A pinion gear can engage internal axial teeth of the right and left deflection racks and rotate when there is relative motion between the racks. A clockwise rotation of the articulating knob could result in a translation along a linear path of the right deflection rack relative to the left deflection rack in a first direction, tensioning a wire or other control element. Similarly, a counterclockwise rotation of the knob could result in a second relative linear translation in a second direction opposite the first direction, tensioning the same or a different wire or control element.

Features, such as relief notches or detents, could be machined into various components of the handle, such as the knob, drive bolt, drive housing, or barrel nut, at various axial or clocking positions to serve as engagement points for selectively maintaining certain tip deflections or radial sizes of the expansion element. Alternately, elements can be used to create a friction lock to hold the position of the articulating knob relative to the handle to prevent inadvertent motion during a procedure. These elements can be rubber seals, grommets, or other common components known in the art. The knob assembly can thus be capable of maintaining certain angular and longitudinal positions as they correspond to desired discrete deflections or radial sizes of the expandable element.

In another example, a handle section to control a steerable catheter can include a deflection thumb knob allowing for bi-directional deflection, a balloon disposed around or connected with a distal portion of the catheter body, a balloon advancement mechanism, and a luer fitting for balloon inflation and irrigation. An additional luer fitting can be located approximate the distal end of the handle section with a lumen extending through the handle, catheter body, advancement mechanism, and balloon and be in fluidic communication with the distalmost tip of the catheter. This luer fitting and lumen can serve as an entry port for guidewires or other small devices, as well as supplying irrigation and contrast injection distal to the balloon of the catheter.

Also provided is an example method for controlling a steerable catheter with a control handle during an intracardiac procedure. The method can include some of the following steps presented in no particular order. The example can include introducing a steerable catheter into the vasculature, the catheter comprising a catheter shaft having a proximal region, a deflectable distal region, and a control handle. The control handle could have an outer shell, a distal knob assembly capable of linear translation along and rotation about a longitudinal axis of the handle, and a drive assembly movably disposed in the outer shell. The drive assembly could have an inner housing, a distal drive bolt, and a split piston carriage threadably engaged with the distal knob assembly.

The distal knob assembly can be linearly displaced along the longitudinal axis to actuate the expansion or retraction of an expandable element on the distal end of the steerable catheter. In an example, linearly displacing the knob proximally with respect to the outer shell can increase the radial size of the expandable element while a corresponding displacement distally can decrease the radial size. Rotation of the distal knob assembly about the longitudinal axis can cause an angular deflection of the steerable tip by activating control members which can be coupled to the drive assembly. Clockwise rotation of the knob could deflect the tip one direction, while a corresponding counterclockwise rotation could deflect the tip along the same plane in the opposite direction.

The method steps involving rotation and translation of the distal knob assembly could occur independently of one another. For example, for ease of delivery to a site targeted for ablation, the knob could be positioned so that the expandable element assumed a small radial size. Upon reaching a site just proximal of the target, the expandable element could be expanded to a desired larger radial size based on the size of the patient's ostium through proximal translation of the knob. Thus, the expandable element, such as an ablation balloon with independently controlled electrodes around its circumference, can be prepared for a procedure without tip deflection or contact with the tissue. The desired radial size of the expandable element can then be maintained while the final steering adjustments are made by rotating the knob to deflect the distal tip into position.

Furthermore, the handle can be held in one hand while the deflection and rotation of the knob are performed by the thumb and fingers of the same hand. By not needing the other hand, the user does not need to look away from the procedure to reference the position or orientation of the handle, and attention can be kept on the associated monitoring equipment of the procedure.

The method can further include the step of including internal physical stops or another similar method of limiting the translational travel, rotational travel, or both the translational and rotational travel of the knob assembly of the handle. Limits can be placed so that a physician can be aware of the absolute travel capabilities and performance of the catheter prior to and during the procedure. For example, knowing these limits can be advantageous in situations where the deflection of the tip is out of plane with the physician's own viewing angle. Intermediate axial positions of the knob could also be configured to correspond to discrete radial sizes of the expandable element so the expandable element can conform to different anatomy geometries.

Another method for manipulating a distal tip of a catheter with only one hand can have the step of positioning a catheter in the vascular. The catheter can have an elongated tubular member with a manipulatable distal tip and a control handle proximal of the elongated tubular member. The control handle can have an outer housing and a control knob configured for translational and rotational motion relative to the outer housing. Internal to the outer housing can be a control assembly coupled with the control knob such that linear displacements and angular rotations of the control knob actuate control functions of the distal tip of the catheter.

The actuation could happen through multiple methods, such as the tensioning of control wires and/or the use of a columnar member to exert axial thrust loads on a part of the distal tip of the elongated tubular member. When the tip has been positioned at a location proximal to a target location, the control knob can be linearly displaced along a longitudinal axis of the housing to expand and deploy an expandable element at the distal tip. Grooves or recesses could be configured into the handle to allow the control knob to maintain certain intermediate discrete angular or axial positions. The element could take a number of forms, such as a balloon with multiple independently controlled electrodes configured around its circumference for ablation of the pulmonary veins. To further direct the tip, the control knob could be rotated clockwise to deflect the distal tip on a first direction or rotated counterclockwise to deflect the tip in a second direction opposite the first direction.

A plurality of independently controlled electrodes can be spaced around the circumference of the expandable element. The expandable element can be maneuvered into circumferential line contact with the walls of a pulmonary vein, and the tissue around the line contact can be ablated by directing energy through conductors from an energy source, such as an RF generator, to the electrodes. A further step could involve using the control handle to direct the tip to separate subsequent ablation locations during the procedure. Once the ablation has been concluded, the control knob of the handle could be linearly displaced distally to collapse the expandable element into a smaller radial size so that it could be re-loaded into a sheath or outer catheter for extraction from the patient.

In addition to those listed here, additional steps could be included as would be appreciated and understood by a person of ordinary skill in the art. The example method can be performed by an example control handle as disclosed herein, a variation thereof, or an alternative thereto as would be understood by a person of skill in the art.

Other aspects and features of the present disclosure will become apparent upon reviewing the following detailed description in conjunction with the accompanying figures.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 3 is a top view of the control handle of FIG. 2 according to aspects of the present invention;

FIG. 4 is a side view of the control handle of FIG. 2 according to aspects of the present invention;

FIG. 8 is a cross-section view from the top of the control handle showing the handle interfaces with the drive housing according to aspects of the present invention;

FIG. 9 is a magnified section view of the cross-section view from FIG. 8 showing the coupling of the barrel nut and piston carriage according to aspects of the present invention;

FIGS. 17a and 17b show an example of the expandable ablation balloon as operated by the advancement mechanism in its delivery configuration and expanded deployed configuration, respectively, according to aspects of the present invention;

FIGS. 20a through 20f are a sequence of cutaway views showing how different displacements and rotations of the articulating knob operate the functions of the distal tip of the steerable catheter, according to aspects of the present invention;

DETAILED DESCRIPTION

Specific examples of the present invention are now described in detail with reference to the Figures, where identical reference numbers indicate elements which are functionally similar or identical. The figures illustrate a control handle for a steerable catheter which can be operable with one hand to improve ergonomics for the operator while controlling steerable and expandable functions of the distal tip of the catheter. The articulating knob of the control handle functions with consistency regardless of the orientation of the handle, with the ergonomic movements allowing the user to comfortably keep their attention on the monitoring equipment while conducting a procedure. These improvements can lead to safe and more rapid procedure times.

Although often mentioned herein in the context of ablation procedures, it can be appreciated that the control handle disclosed can be applicable to catheters with activated tip mechanisms for a variety of procedures, such as mapping or diagnostics. Accessing the various vessels within the vascular, whether they are coronary, pulmonary, or cerebral, involves well-known procedural steps and the use of a number of conventional, commercially available accessory products. These products, such as angiographic materials, rotating hemostasis valves, and guidewires are widely used in laboratory and medical procedures. When these products are employed in conjunction with the system and methods of this invention in the description below, their function and exact constitution are not described in detail. While the description is in many cases in the context of cardiac ablation treatments, the systems and methods may be used for other procedures and in other body passageways as well.

A steerable catheter or sheath may be utilized to gain access to a target location within the body. Such devices can have control mechanisms to provide access to areas of the body through the vasculature using minimally invasive procedures. In some of these procedures a tip of the catheter or sheath may be required to provide access by deflecting in more than one direction. In other procedures, the tip may require expandable functions at the target site.

Figure 1:
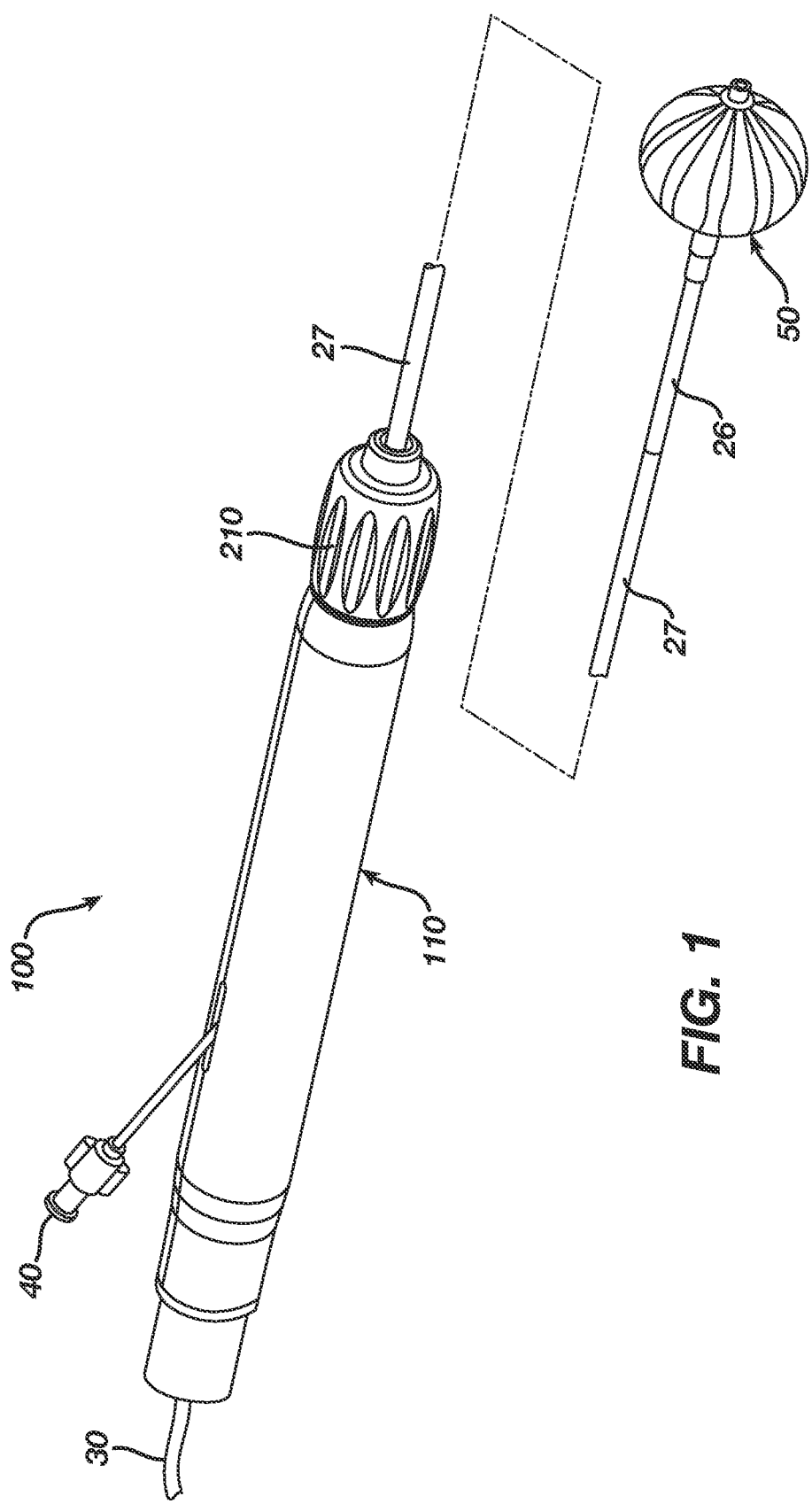
FIG. 1 is a system-level view of a control handle operable with one hand and capable of actuating multiple functions of the distal tip of a steerable catheter, according to aspects of the present invention.

Turning to the figures, FIG. 1 illustrates a steerable control system or handle 100 for manipulating medical devices while conducting intravascular procedures. The medical device could include, by way of example, a catheter, sheath, introducer, or similar devices. Such devices are often used for cardiac ablation, mapping, diagnostics, thrombectomy, and other procedures. The handle 100 can be coupled with a catheter shaft or sheath 27 to enable a user to direct and steer the shaft using the handle. The handle 100 can comprise an articulating knob 210 coupled to the outer shell or housing 110. The knob 210 can be rotated and linearly translated independently with respect to the outer shell 110 of the handle. The handle 100 can further have connections for a catheter cable 30 coupled to a function generator or the diagnostics hub of a navigation system to send and/or receive data during the procedure.

In some instances, the handle 100 can have one or more luer fittings 40 for fluid injection through the outer housing 110 using a syringe, pump, or other means. The fluid can be a contrast media, saline, or other solution and can be used for any of a number of purposes depending on the procedure. These can include angiography, irrigation, cooling, or the inflation of balloons or other inflatable members.

In use, the rotation of the articulating knob 210 in a first clockwise rotational direction with respect to the outer housing 110 of the handle 100 can allow a user to deflect and steer a deflectable segment 26 of the catheter shaft 27. Similarly, rotation of the knob in a second counterclockwise rotational direction can allow deflection and steering in an opposite direction. In other examples, the bi-directional steerable catheter is configured to deflect in two separate deflection directions which are out of plane with each other.

The linear deflection of the articulating knob 210 with respect to the outer housing 110 of the handle 100 can control another function of the steerable distal tip 50 of the catheter. For example, the degree of axial displacement proximally or distally could change the radial size of an expandable element of the steerable tip so that it could be deployed from a smaller delivery configuration to an extended deployed condition which could be necessary for conducting a particular procedure. Upon the need to reposition the catheter tip 50, or at the conclusion of the procedure, an axial displacement in the opposite direction from that used to expand the element can be applied to revert the element to a smaller size or profile for maneuverability.

Figure 2:
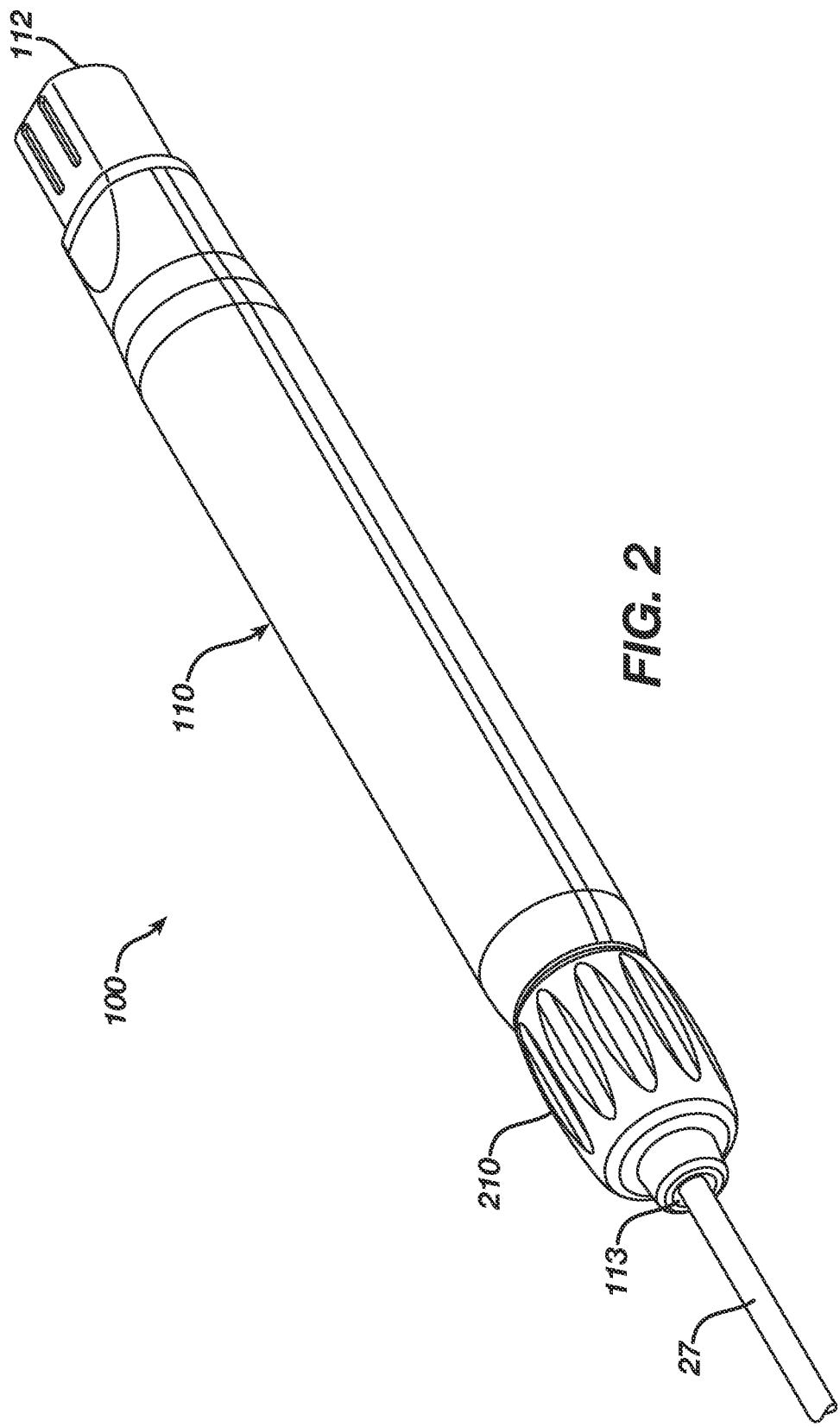
FIG. 2 is an isometric view of a control handle according to aspects of the present invention.

FIGS. 2-4 show different orientation views of a control handle design. Referring to FIG. 2, the outer housing 110 of the control handle 100 can be a generally tubular shape. The catheter shaft 27 can extend through the distal end 113 of the handle 100. The articulating knob 210 can be disposed distal to the outer housing 110 such that when the handle is held in the palm of the hand, all functions of the knob can be operated using the thumb and/or forefingers of the same hand. The catheter shaft 27 can be extend internal to the outer housing 110 such that the shaft is not impinged by the knob and the knob is free to translate and rotate along its full range of motion. The proximal end 112 of the handle 100 can have further fittings or entranceways for other ancillary devices needed for a desired procedure, or for further fluid injection for irrigation and/or contrast.

Elements visualized in the figures can be described as tubular structures and are generally illustrated as a substantially right cylindrical structure. However, when used herein, the terms "tubular" and "tube" are to be construed broadly. They are not meant to be limited to a structure that is a right cylinder or strictly circumferential in cross-section or of a uniform cross-section throughout their length.

The outer housing 110 of the handle 100 can be divided into halves for manufacturing and assembly as seen in FIG. 4. The housing can have an upper shell 120 and a lower shell 130, which may or may not be equal in radial size and can be secured together into an enclosure by fasteners, snap-fit, adhesives, or other suitable means. The outer housing 110 can encase the actuation of all of the handle's control functions so there are no sharp edges or buttons for snagging and so the articulating knob 210 is the only moveable control surface.

Figure 5:
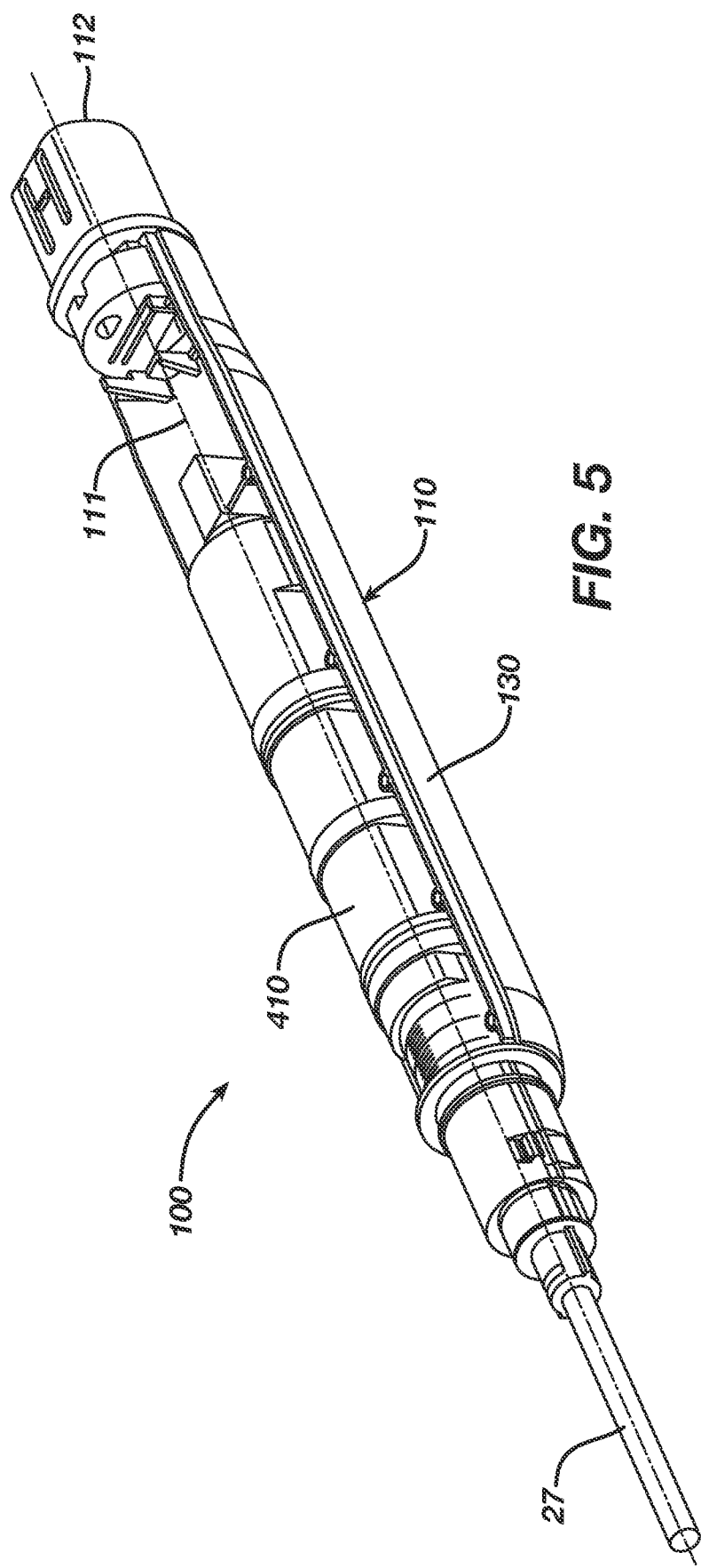
FIG. 5 is an illustration of the control handle with the top section of the outer housing removed according to aspects of the present invention.

Referring to FIG. 5, the outer housing 110 provides a hollow shell for enclosing the drive housing 410 and allowing linear translation of the drive housing therein along the longitudinal axis 111. This figure depicts the assembly with the articulating knob 210 and the upper half of the outer housing removed, with the drive housing 410 disposed within and sharing the longitudinal axis 111 with the outer lower shell 130. The drive housing can be axially coupled to the articulating knob so that linear translation of the drive housing within the outer housing is driven directly by the linear translation imparted on the articulating knob by the user. The catheter shaft 27 can be coupled proximally within a part of the drive housing 410 so that it is controlled by the rotation and translation motions of the handle 100. The handle can terminate at a proximal end 112 which could be used to interface with cabled connectors or additional luer fittings for irrigation or contrast injection. Alternately, the proximal end 112 could have a secondary entry point for a guidewire or similar small diameter device.

Figure 6:
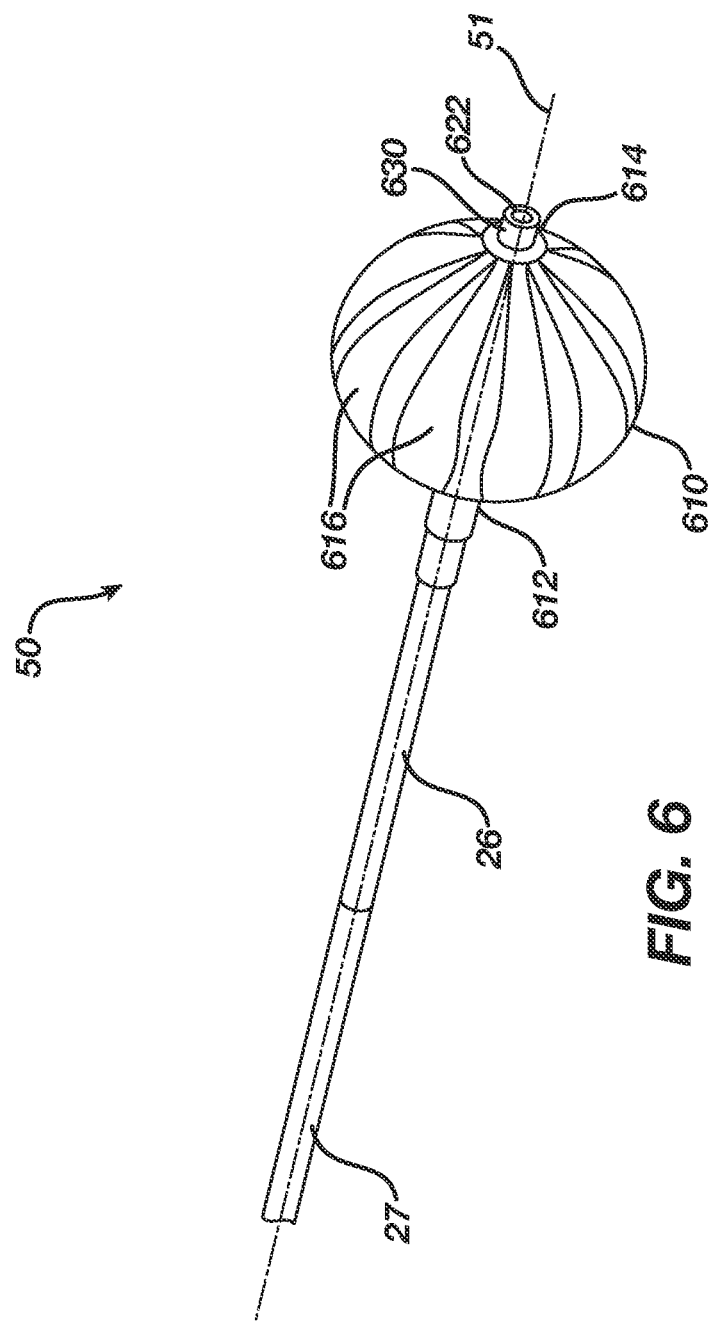
FIG. 6 is an example of an expandable ablation balloon capable of being both expanded and deflected by the control handle according to aspects of the present invention.

The distal tip 50 of the catheter can take a number of forms depending on the needs of the procedure to be performed. The handle 100 can be beneficial for any distal tip design which can expand and collapse or change the morphology of its shape. In one example, the tip could have an expandable cage or basket-like structure or be configured to monitor and map cardiac signals for diagnostics. In another example, the catheter could be adapted to deliver energy for cardiac ablation. The distal tip 50 of the catheter in this example could be an expandable balloon ablation system, as seen in FIG. 6 and described in aforementioned U.S. Pat. Publication No. 2016/0175041. In this example, a compliant balloon 610 can be used for isolating the pulmonary veins in a subject's left atrium. The balloon 610 can expand to a largely spherical or ovular shape about the longitudinal axis 51 of the tip 50. The distal end 614 of the balloon can taper down into atraumatically into an extension collar 630 approximate the distal end of the balloon.

A lumen 622 can extend through the catheter shaft 27, balloon 610, and extension collar 630. The lumen 622 can allow access distal to the ablation site and can serve as a delivery channel for distal irrigation, contrast injection, and/or for guidewires and other small diameter devices. For example, a lumen diameter of 0.050" could accommodate guidewires up to 0.035" while capable of maintaining irrigation through the lumen 622 to prevent blood clots.

A high-torque shaft 27 can allow the steerable catheter tip 50 to have the deliverability characteristics and level fidelity required for precision procedures. The shaft could transition distally into a steerable deflectable tip segment 26 controlled by the handle 100. Internal to the tip segment 26, and not shown in FIG. 6, can be lead wires for the electrodes 616 and control elements for deflection of the tip 50.

Some or all of the catheter shaft 27 or tip 50 could also have additional features for deliverability and torque transmission, such as directional braids or selective-modulus polymeric jackets. The high-torque shaft allows the plane of the deflected tip to be rotated for facilitating accurate positioning at a target site, such as the ostia of the pulmonary veins. The torque transmission capability is also useful when the catheter tip has a balloon with circumferential electrodes, but whose shape may otherwise limit translation in certain directions when deployed. The stiffness and torque properties of the shaft 27 add smooth pushability while the flexible compliance of the balloon 610 allows for atraumatic conformance of the balloon 610 with the local tissue anatomy so that the circular arrangement of electrodes 616 can achieve the appropriate contact with the vein ostia.

The outer surface of the balloon 610 could have a plurality of independently controlled electrodes 616 bonded to the surface of the balloon and oriented circumferentially to create a circular contact profile with the pulmonary vein ostia. The shape of the electrodes can be chosen to enable similar electrode-to-electrode spacing axially over the changing diameter of the expanded balloon between the proximal end 612 and distal end 614. Each electrode can be gold-plated for conductance and perforated with individual holes permitting fluid flow from the inside of the balloon to the outside. For example, heparinized saline can be delivered through a luer fitting 40 of the handle 100 for irrigation flow.

The electrodes 616 can extend from the proximal end 612 to the distal end 614 of the balloon 610 in a flexible circuit. Having the electrodes independently strung in this fashion allows for each electrode to have a conductor, such as a bifilar wire, to be routed through the catheter shaft 27 to independently deliver energy and serve as a thermocouple for detecting temperature at each electrode interface. The energy could be delivered using RF, cryogenic, IRE, or other similar techniques.

Figure 7:
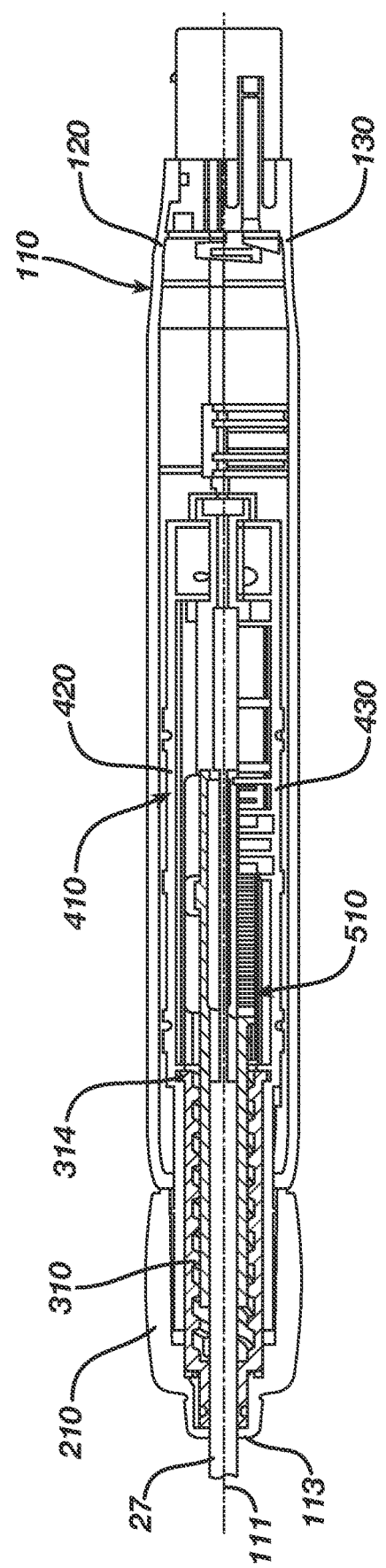
FIG. 7 is a cross-section view from the side of the control handle showing the handle interfaces with the drive housing according to aspects of the present invention.

A cross-sectional side view of the handle from FIG. 3 is illustrated in FIG. 7. The articulating knob 210 can be axially secured to the drive housing 410 such that they translate as a pair, such as with a collar, retaining ring, or set screws. In the example in FIG. 7, a thrust collar 314 can transmit push/pull forces between the knob and the drive housing. When secured in this way, as the knob is displaced distally or proximally along the longitudinal axis 111 relative to the outer housing 110, the same displacement is experienced by the drive housing. Alternately, a portion of the articulating knob could extend proximally to be received into the drive housing, where it could be secured via a set screw or other means. The outer housing 110 can be configured so as to guide the linear displacement of the drive housing 410, while also restricting or limiting the total travel range available to the drive housing. Since they can be coupled, this limitation on displacement of the drive housing 410 can also be experienced by the articulating knob 210.

A linear deflection of the articulating knob 210 of the handle 100 can be converted into the expansion or retraction of an expandable element via movement of the drive housing 410 within the outer housing 110. Alternatively, a linear deflection of the articulating knob 210 can be used to deflect the catheter tip in a direction related to the induced relative motion of the drive housing 410. Actuation of the expandable element from the control handle can offer procedural advantages and eliminate the need for separate expansion mechanisms to be incorporated with the handle for this purpose. For example, as seen in FIG. 6, the proximal end 612 or the distal end 614 of the balloon 610 can have an extension collar 630 which can be slidably disposed along the tip axis 51 and longitudinally coupled to the drive housing 410 within the handle 100. In this configuration, linear translation of the drive housing in a first direction could increase the radial size of the balloon, while translation of the drive housing in a second direction opposite the first direction could decrease the radial size of the balloon.

The rotations of the articulating knob 210 of the handle 100 can be converted into angular deflections of the catheter shaft 27 or expansion of an expandable member at the catheter tip 50 via relative movement of the drive housing 410 within the outer housing 110. A piston carriage 510 in the drive housing 410 can have an externally threaded arrangement which is received within a barrel nut 310 having a corresponding internally threaded arrangement and which is rotatably coupled to the articulating knob 210. The threads allow the knob 210 to linearly translate the piston carriage 510 in the drive housing 410 as the knob is rotated.

In one example, the piston carriage 510 can have multiple parts that cooperatively engage or can be assembled to form the carriage. As shown in the cross-sectional views of the handle 100 in FIG. 8 and FIG. 9, the carriage can have a right deflection rack 530 half and a left deflection rack 540 half which are linearly translatable along the longitudinal axis 111 within the drive housing 410. Distally, the piston carriage can have a bolt with a right half 520 and left half 521, at least one of which can have external male threads 522.

In one example, the threads 522 of the right deflection rack 530 of the piston carriage 510 are engaged with helical drive threads 316 of a barrel nut 310. If the right and left deflection racks 530, 540 are restricted from rotation within the drive housing, the drive threads of the barrel nut can act in a linear fashion upon the threads 522 of the right deflection rack. As illustrated in FIG. 9, rotation of the articulating knob 210 and barrel nut 310 about the longitudinal axis 111 can cause a corresponding linear translation of the right deflection rack 530 relative to the left deflection rack 540 within the drive housing 410 by driving the external threads 522 of the right deflection rack.

This rotation of the articulating knob 210 and the resulting relative translation between the right 530 and left 540 halves of the piston carriage 510 can be a mechanism for the actuation of the aforementioned control members (not shown). Actuation of the control members can occur, for example, through the tensioning of wires, or the compression of a toggling element.

The control members can extend through the catheter shaft 27 and cause deflections of the distal catheter tip 50. For example, proximal translation of the right deflection rack 530 relative to the left deflection rack 540 can tension a control wire or cable coupled to the distal end of the catheter and cause the steerable tip to deflect angularly in a first direction (relative to a starting, or neutral, position). Similarly, distal translation of the right deflection rack 530 relative to the left deflection rack 540 could tension a second control wire or cable and cause the steerable tip to deflect angularly in a second direction opposite the first direction.

Figure 10:
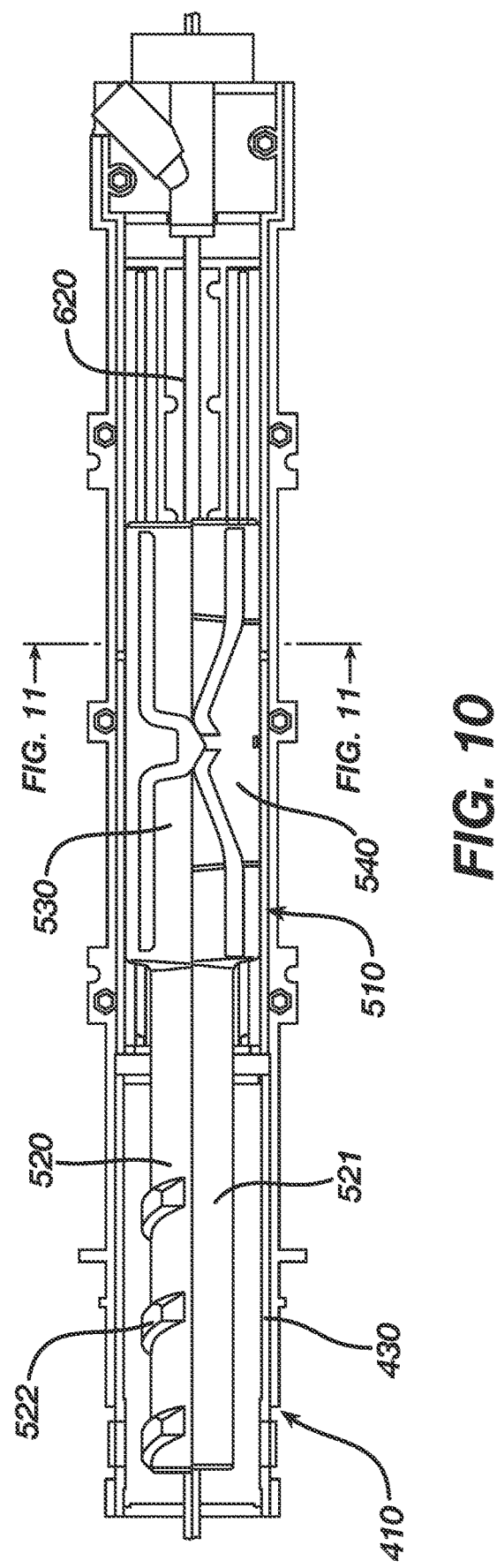
FIG. 10 shows the drive housing and piston carriage of the control handle without the outer housing, articulating knob, or barrel nut according to aspects of the present invention.
Figure 11:
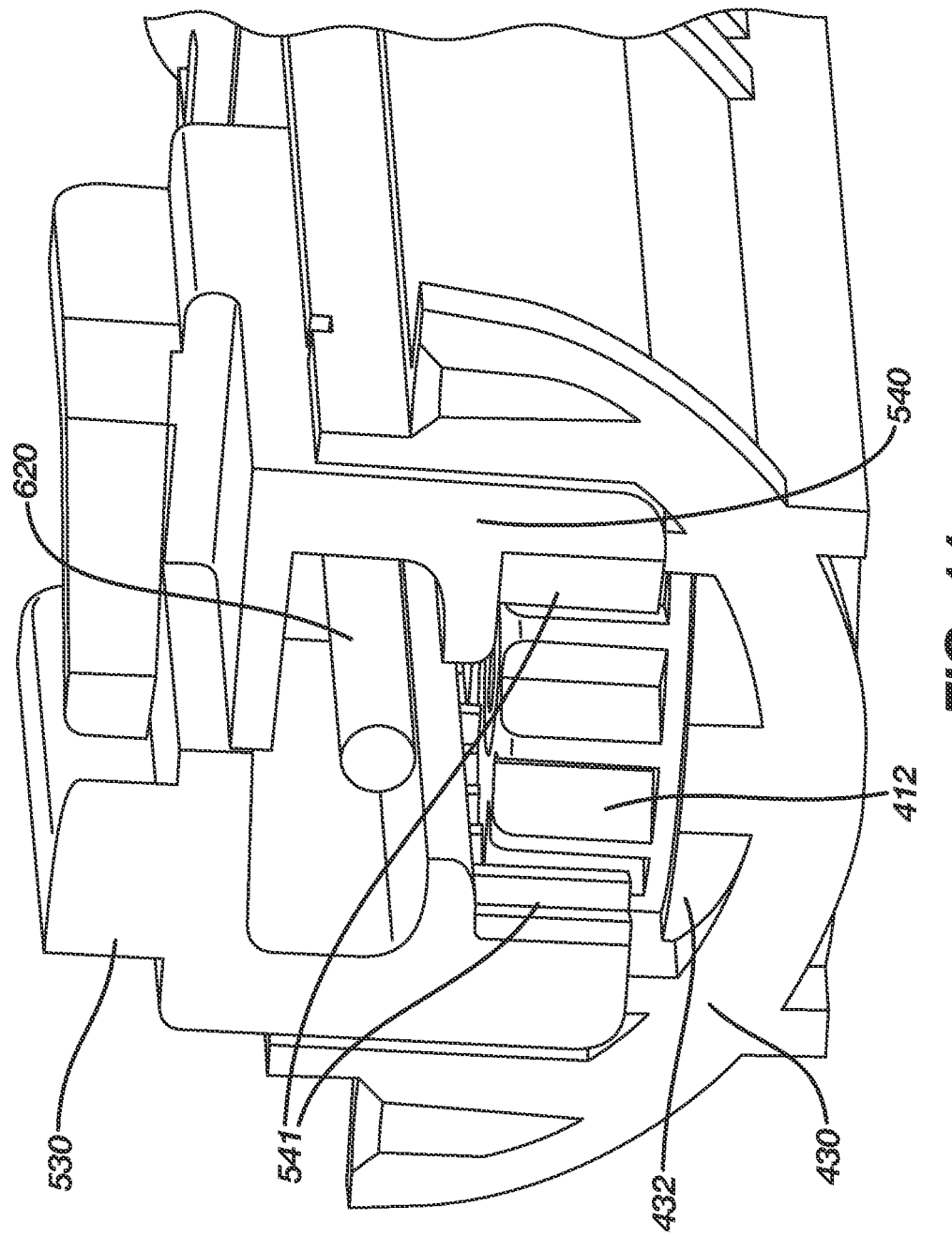
FIG. 11 is a cross-section view from FIG. 10 just distal of the pinion according to aspects of the present invention.

FIG. 10 shows the bottom half 430 of the drive housing 410 with the piston carriage 510 disposed therein. Depending on the configuration there are multiple ways to configure the relative motion of the right and left deflection racks 530, 540 of the piston carriage 510 to impart separate and individual tension forces the aforementioned control members (not shown). In one configuration, control wires can be directly coupled to the opposing halves of the piston carriage 510. In an alternative configuration, one of the wires could be directly coupled to the piston carriage while the other wire is indirectly coupled to the piston carriage through a direction-reversing element, such as a pin or pulley (not shown). In this way, both wires are kept in taut and relative motion of the right deflection rack 530 relative to the left deflection rack 540 in one direction will apply tension to one of the control wires while relative motion in the opposite direction will apply tension to the other control wire. An equal and opposite translational motion between the right and left deflection racks 530, 540 can be maintained through the use of a pinion gear 412 coupled to teeth 541 of the deflection racks, as shown in the cross-sectional view in FIG. 11.

The coupling of the control members with the halves of the piston carriage 510 allows for the relative motion to actuate the control members. In this sense, a "direct coupling" would mean a control wire forms an operable pair with but is not necessarily attached to or integral with one of the deflection racks. An "indirect coupling" could mean a wire forms an operable pair with (but is similarly not necessarily attached to) one of the deflection racks only after passing through an intermediate element, such as a pulley. The wires could be maintained within a sheath along most of their length or one or more strain relief methods employed to ensure they are not subjected to excessive angulations or stresses when coupled to the piston carriage 510.

Figure 12A:
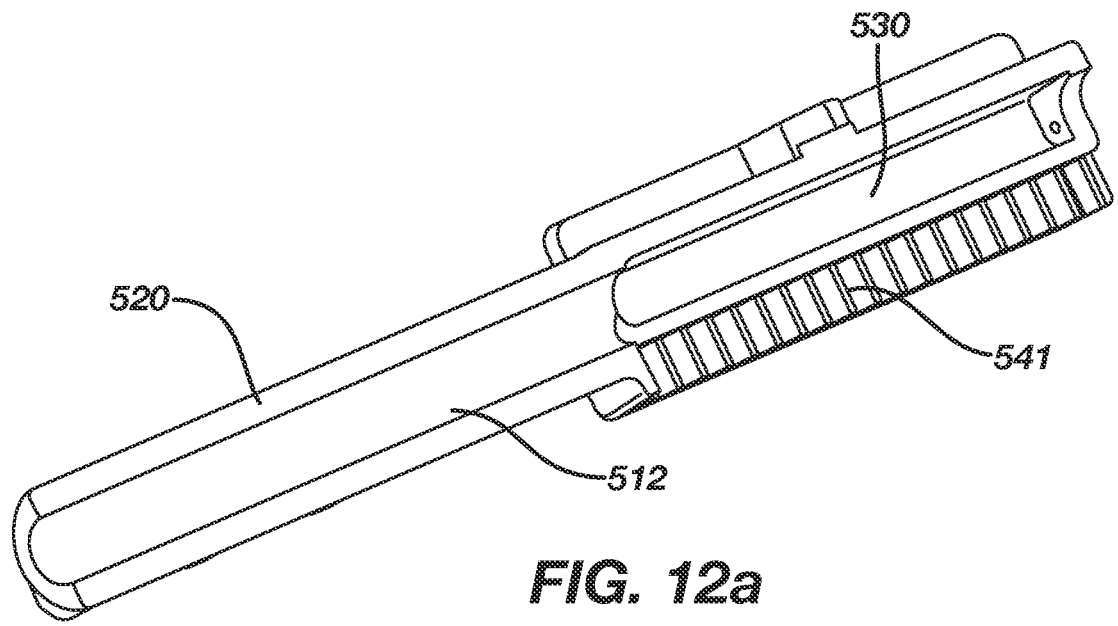
FIGS. 12a and 12b illustrate the right and left deflection racks, respectively, according to aspects of the present invention.
Figure 12B:
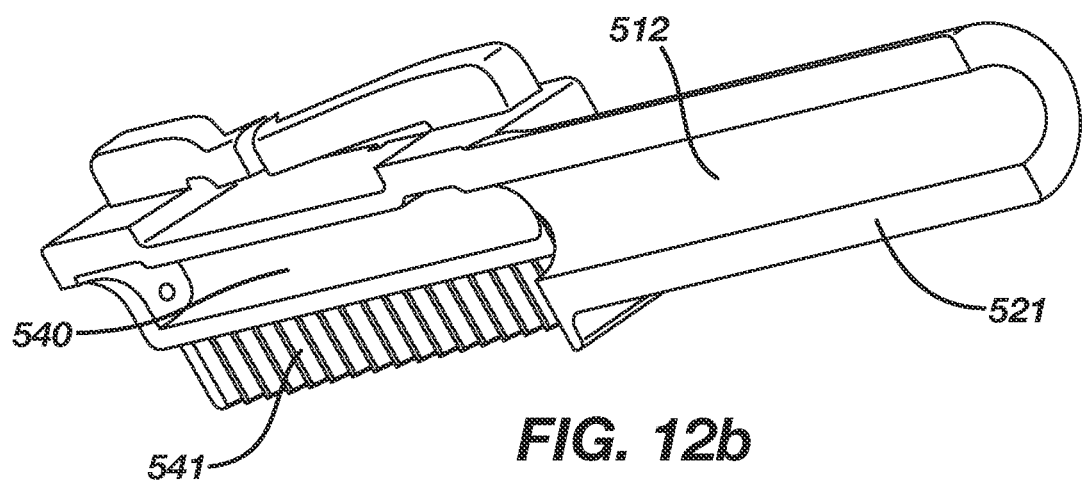

Independent views of the right deflection rack 530 and left deflection rack 540 are shown in FIG. 12a and FIG. 12b, respectively. When mated together, the right drive bolt half 520 of the right deflection rack 530 and the left drive bolt half 521 of the left deflection rack 540 can form a cylindrical inner cavity 512 for the catheter sheath to extend therethrough. From the section view of FIG. 11, the pinion 412 can ensure that there is no relative slip between the right deflection rack 530 and left deflection rack 540 by engaging with the corresponding inner teeth 541 of both deflection racks simultaneously. By metering the relative translation of the right deflection rack and left deflection rack, the pinion teeth provide consistent and repeatable relative deflections for incremental rotations of the articulating knob 210. These deflections can be transmitted to the control members of the handle. A specific magnitude of angular rotation of the articulating knob 210 can correspond with a specific magnitude of linear translation of the right deflection rack 530, which could therefore induce in a specific angular deflection of the steerable tip 50 of the catheter. The rotation of the pinion ensures that the tip deflections occur in a smooth and reliable fashion, such that an experienced physician can comfortably operate and manipulate the catheter with the control handle without the need for visual reference checks of the handle's orientation.

Figure 13:
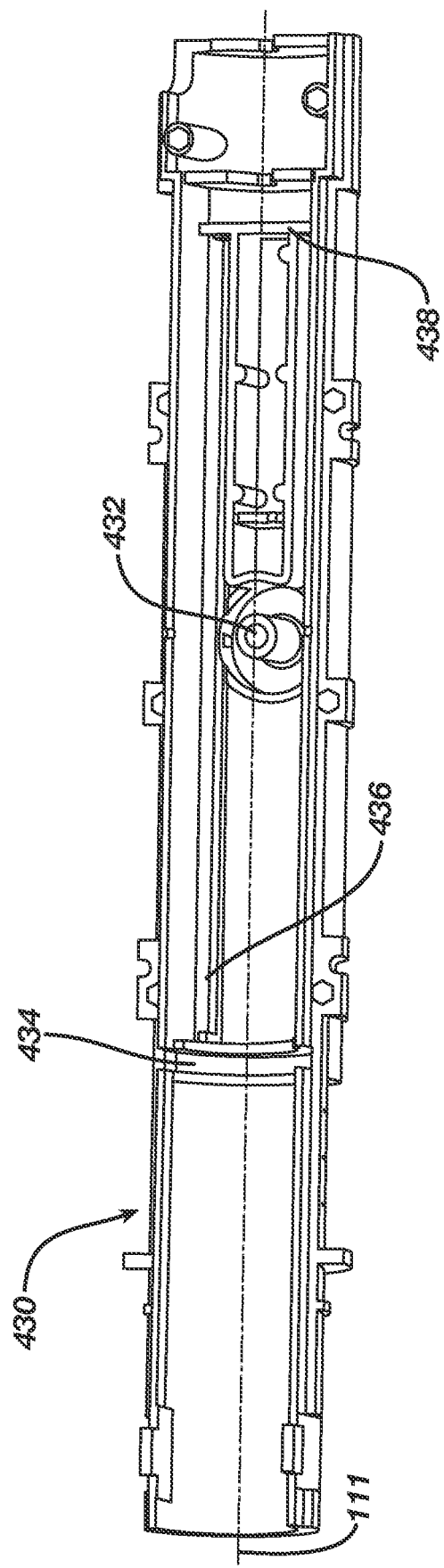
FIG. 13 shows the bottom half of the drive housing of the control handle according to aspects of the present invention.

An example profile of the lower half 430 of the drive housing 410 is illustrated in FIG. 13. At least a portion of drive housing lower half 430 can have longitudinal grooves or rails 436 formed into its interior which form a track to guide the deflection of and serve as anti-rotation features for the right deflection rack 530 and left deflection rack 540 of the piston carriage 510. The rails 436 can react against rotational torques generated from rotation of the articulating knob 210 so that motion of the deflection racks is linear along the longitudinal axis 111 of the handle. The drive housing lower half 430 could also have a pinion hub 432 to locate and provide a spindle for the pinion 412. Additionally, distal-facing features molded into the drive housing lower half 430 can form a terminal or physical stop 438 for the proximal translation of the deflection racks 530, 540. As an alternative, an adjustable length physical stop could be installed to define the extreme travel range of the deflection racks. The length could be adjustable by a screw, or through the use of shims. Any method, such as adhesives or a press-fit, could be used to engage the physical stop with the rails 436 of the drive housing 410.

Linear displacement of the drive housing 410 itself can be controlled through the axial placement of a circumferential groove or thrust slot 434. The thrust slot can be sized to receive the collar 314 of the barrel nut 310 to provide transmission of the push/pull forces a user imparts on the knob 210 to the drive housing. Since the barrel nut 310 is a fixed length, the longitudinal placement of the thrust slot can 434 can define the linear travel range afforded to the articulating knob. For example, a more proximally located thrust slot 434 would locate the barrel nut 310 closer to the proximal end 112 of the handle 100. This location could allow for a greater length of travel for the drive housing 410 within the outer housing 110.

Figure 14A:
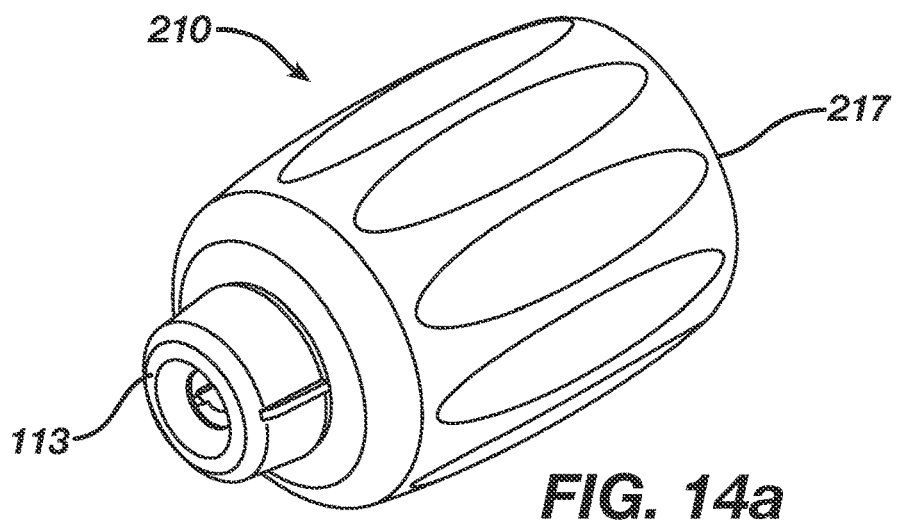
FIG. 14a is an isometric view of the articulating knob of the handle according to aspects of the present invention.
Figure 14B:
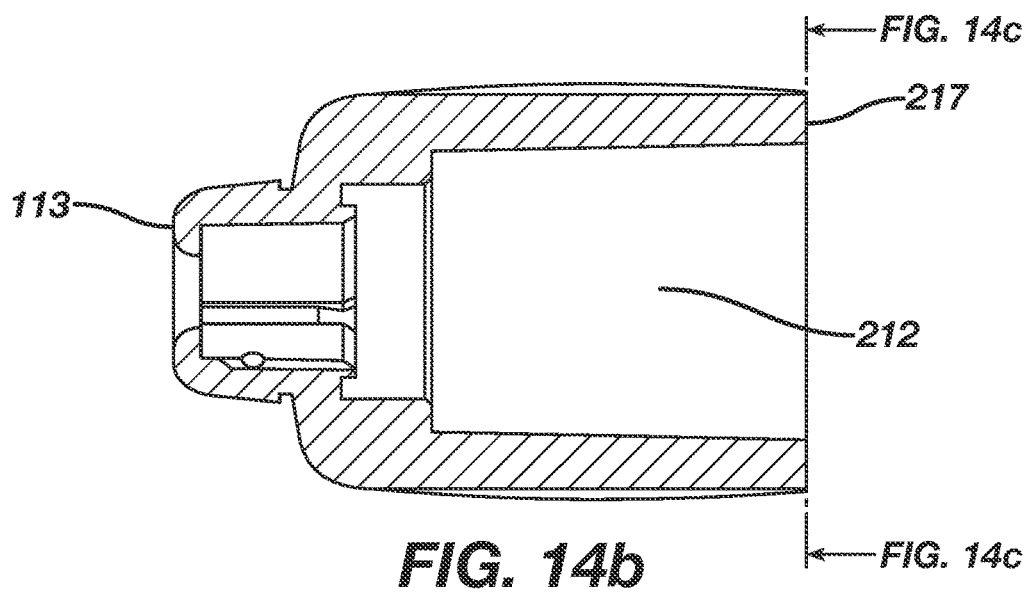
FIG. 14b is a cross-section view of the articulating knob according to aspects of the present invention.
Figure 14C:
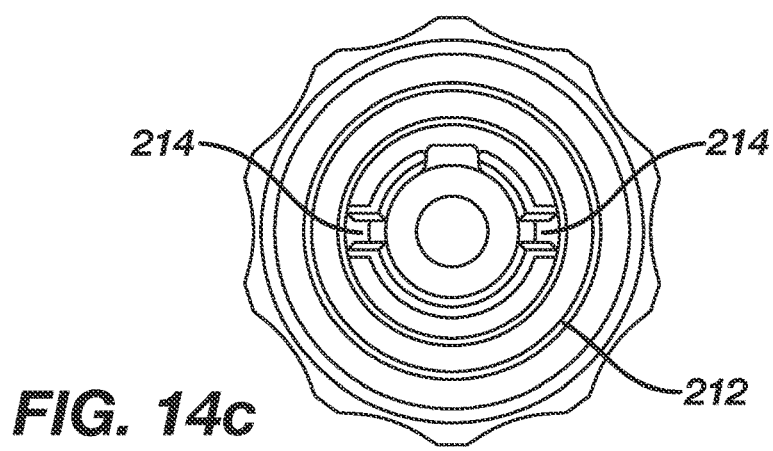
FIG. 14c shows a view of the articulating knob from the proximal end according to aspects of the present invention.

Representative views of an articulating knob of the present design and its various features are shown in FIGS. 14a-c. The knob can be cylindrical or similar shape and can have ridged, overmold, or other contour features in the exterior surface to give the user a more secure grip with the thumb or thumb and forefingers of the operating hand. The knob 210 can taper at the distal end 113 for passage of the catheter shaft 27. The distal end 113 can be beveled with gentle edge radii so as to allow free translation and rotation of the knob while not having sharp corners which could kink or damage the shaft.

Referring to FIGS. 14b and 14c, the interior of the articulating knob 210 can have a knob hub 212 for interfacing with the barrel nut 310 or other component features of the handle 100. Rotation can be transmitted from the knob to the barrel nut through one or more keyways 214 formed into the interior of the hub. They keyway could be tapered or square, and the length could vary based on the size of the hub and the torsional load to be transferred. As an alternative, the knob hub 212 could be shrunk-fit onto the barrel nut 310.

Figure 15:
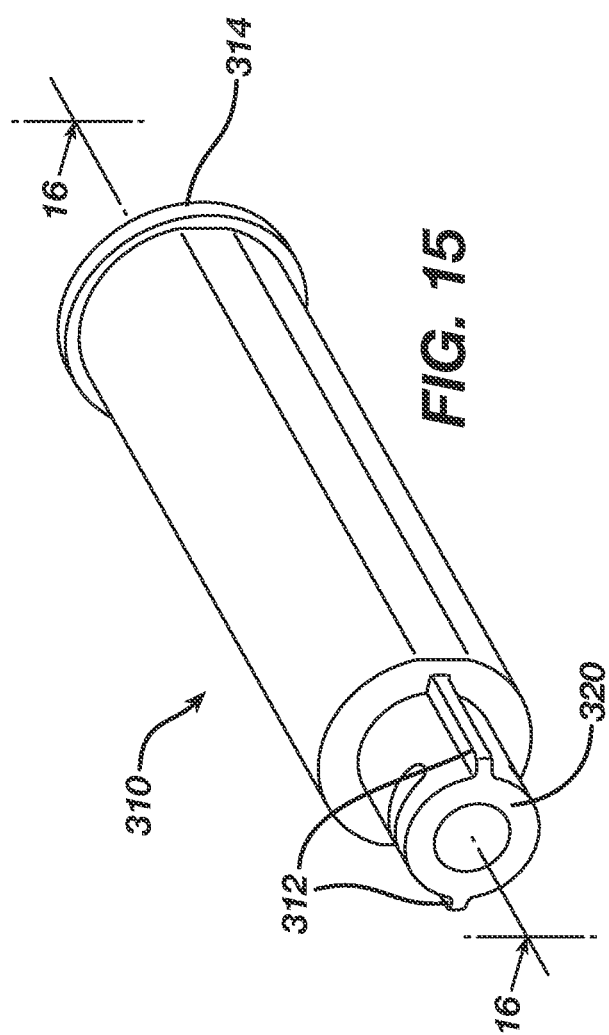
FIG. 15 is an isometric view of the barrel nut of the handle according to aspects of the present invention.
Figure 16:
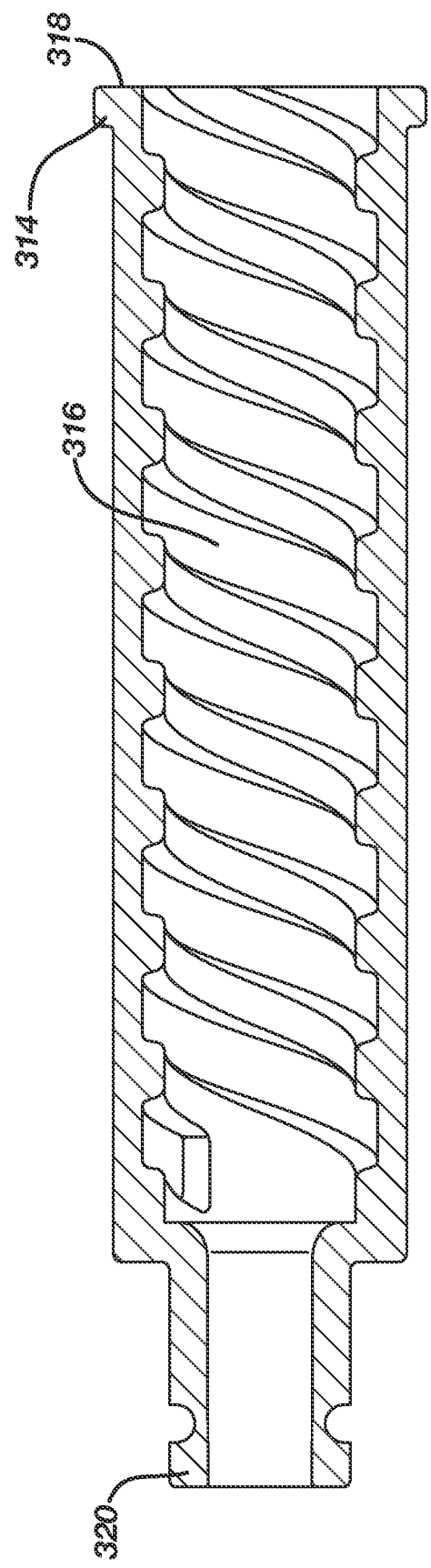
FIG. 16 is a cross-section view of the barrel nut according to aspects of the present invention.

FIGS. 15 and 16 show a perspective and cross-sectional views, respectively, of the barrel nut 310. The barrel nut can be of a substantially tubular profile and can have a reduced diameter distally for insertion into the interior of the articulating knob 210. In one example, the barrel nut 310 has one or more outwardly extending keys 312 which cooperatively engage with or fit into the corresponding keyways 214 (see FIG. 14c) of the articulating knob. The keys 312 can serve as retention features to prevent relative angular motion and transmit torque between the knob 210 and the barrel nut 310. This couples the barrel nut 310 to be rotated with the articulating knob 210. Thus, rotational and translational motion of the knob 210 is transferred to the barrel nut 310 and they can be operated as a single unit with respect to the outer housing 110 of the handle 100.

Axially, a thrust collar 314 approximate the proximal end 318 of the barrel nut 310 can transfer push/pull forces between the knob and the drive housing 410 by mating with the circumferential slot 434 in the drive housing. The slot 434 and thrust collar 314 can lock the longitudinal translation of the articulating knob and drive housing while permitting free rotational motion of the knob.

Female drive spline threads 316 can be machined or formed into the inner surface of the barrel nut, as illustrated in the cross-section in FIG. 16. As torque is transferred from the articulating knob 210 to the barrel nut 310, the spline threads 316 can engage with the drive bolt threads 522 of the right or left deflection rack 530, 540 of the piston carriage 510 (see FIG. 10). The turning of the spline thus drives a relative linear displacement between the right deflection rack 530 and left deflection rack 540.

Features could be formed or machined into surfaces of the knob hub 212 or surfaces of the barrel nut 310 to function as set points, so that various clocking positions are engaged as the articulating knob 210 is rotated to maintain a particular tip deflection corresponding with a particular amount of angular rotation. These features, such as detents or axial relief notches or grooves, could selectively maintain certain tip deflections and give the knob a "click-in" capability, yielding tactile feedback to the user when certain discrete engagement points were reached.

Alternatively, a friction device, such as a rubber grommet or O-ring, could be used between the barrel nut 310 and the inner surface of the drive housing 410 to create a friction lock increasing the rotational resistance and maintain the articulating knob 210 in a desired rotational position with respect to the axis.

Many expandable elements utilized with steerable catheters require a separate activation mechanism in addition to the steering of the control handle to actuate the expandable element between a collapsed delivery state within a delivery catheter or sheath and an expanded, deployed state at the target site. For example, the expandable ablation balloon 610 shown in FIG. 6 could expand to a deployed shape to provide for atraumatic conformance with the ostium of a pulmonary vein. It is an advantage of the current design to combine the expansion and retraction of a balloon with the steerable functionality of the control handle to control the radial size of the balloon without any additional auxiliary mechanism.

To deliver the steerable catheter tip 50 with an expandable element or balloon 610 within a guide sheath or outer catheter to a target location, it can be necessary to first collapse the balloon 610 and any associated leads and electrodes to a smaller diameter. The collapsed diameter could comply with common guide sheaths of a specific inner diameter, such as 13.8 F. The displacement function of the articulating knob 210 of the handle 100 can articulate an advancement mechanism 620, which could lengthen the balloon from its nominal, near-spherical shape (FIG. 17b) to an elongated football-like profile (FIG. 17a) with a smaller radial size for delivery. This motion can be similar to tubular bellows or an expansion joint whose diameter changes relative to the axial location of its corresponding ends. In one case, the advancement mechanism 620 could be bonded to the distal end of the balloon 614 using adhesives or other suitable means. Alternately, the distal end 614 of the balloon could be bonded to a rigid extension collar 630 to provide a rugged attachment point.

The advancement mechanism 620 can extend proximally the length of the catheter shaft 27 to be coupled to the drive housing 410 in the control handle 100. In this way the advancement mechanism 620 could operate telescopically with the catheter shaft 27 to move the distal end 614 of the balloon 610 distally to provide the elongation necessary to decrease the balloon's outer diameter. The advancement mechanism could be a tube having an internal lumen 622 as for guidewires and other small ancillary devices and a conduit for directing irrigation for cooling and the prevention of blood clots.

The advancement mechanism 620 can have sufficient column stiffness to smoothly transmit thrust loads to translate the distal end of the expandable member, while also having ample transverse flexibility for delivery through the tortuous vascular to a target site. In one example, the advancement mechanism can be constructed of a rugged and chemically resistant polymeric material, such as flexible polyimide tubing. Alternately, the advancement mechanism could be a tubular coiled or looped support structure coated with an outer jacket.

Figure 18:
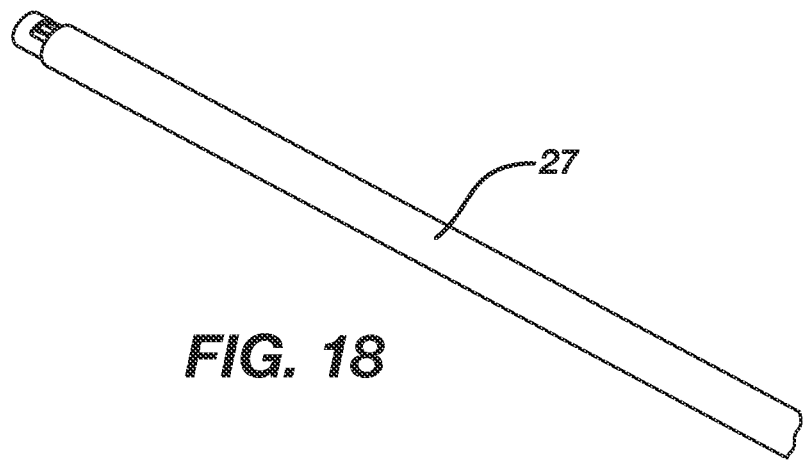
FIG. 18 shows the shaft of the steerable catheter according to aspects of the present invention.
Figure 19:
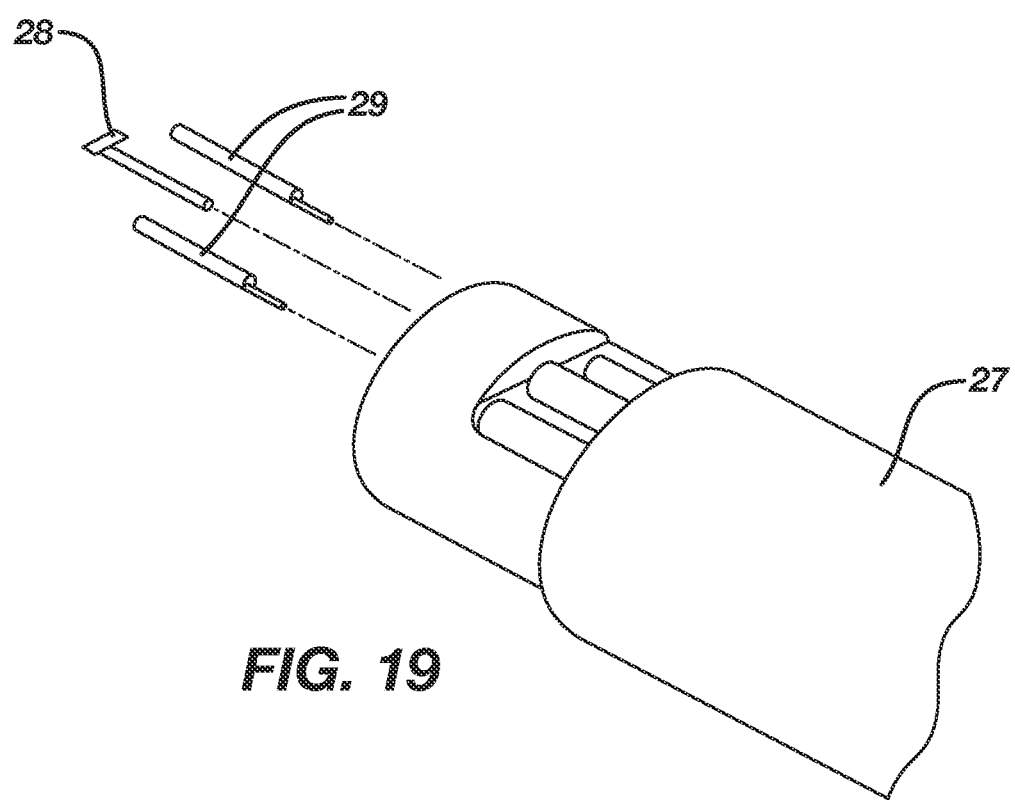
FIG. 19 is a magnified cutaway view of the shaft of FIG. 18 showing some of the internal control elements according to aspects of the present invention.

In one example, the control elements for the deflection of the distal tip could be a pair of control wires 29 that extend substantially along the length of the catheter shaft 27, as shown in FIG. 18 and a corresponding closer representation in FIG. 19. As previously discussed, the wires 29 could be coupled proximally to the right 530 and left 540 deflection racks of the piston carriage 510 within the drive housing 410. The control wires could be constructed of steel or a large molecular weight polymer with sufficient tensile strength to cause the deflections of the tip when the articulating knob 210 is rotated about the axis 111 of the handle.

The wires 29 can be coupled or crimped distally on opposite sides of a cross or T-shaped member 28. Rotation of the articulating knob clockwise can tension a wire joined on one side of the T-shaped member, causing the catheter sheath or shaft 27 to deflect in a first direction relative to a nominal starting position. Similarly, counterclockwise rotation of the knob can tension a second wire affixed on the opposite side of the T-shaped member, deflecting the shaft in a second direction. Direction-reversing elements, such as pins or pulleys, can be used in the handle so that both wires 29 are kept in tension regardless of which direction the knob is rotated.

FIGS. 20a-20f are pictorial representations of a use sequence for a control handle 100 of a steerable catheter with a distal expandable element as described herein. For demonstrative purposes, the catheter is assumed to be configured with an expandable element such as the ablation balloon 610 as shown in FIGS. 17a and 17b. The figures feature a cutaway central portion of the outer housing 110 so that motion of components within the housing as a result of manipulation of the articulating knob 210 can be seen.

FIG. 20a shows the articulating knob 210, drive housing 410, and piston carriage 510 of the control handle 100 in at their most proximal limit of longitudinal travel. The right deflection rack 530 and left deflection rack 540 of the piston carriage 510 are axially aligned, and the drive bolt threads 522 of the right drive bolt half 520 are engaged with the internal threads of the barrel nut 310. The piston carriage can ride along one or more expansion pistons 542 within the housing. Arrows overlaid on the articulating knob indicate the directions of rotation and translation available for articulating the knob.

A distal linear translation of the articulating knob 210 from the nominal starting position of FIG. 20a is shown in FIG. 20b. The thrust collar 314 of the barrel nut 310 can pull the drive housing 410 distally such that the right and left deflection racks 530, 540 of the piston carriage 510 also translate distally along the one or more expansion pistons 542. The distal translation of the knob 210 can push the advancement mechanism 620 and extension collar 630 downstream to decrease the radial size of the balloon 610 (see FIG. 17a). Full distal extension of the knob can completely collapse the balloon for repositioning during the procedure or re-sheathing for retraction from the patient.

Referring to FIG. 20c, the applied distal translation of the articulating knob 210 can be maintained while independently rotating the knob about the longitudinal axis 111. Rotation of the knob 210 can also rotate the barrel nut 310. The helical female threads 316 of the barrel nut 310 can engage and drive the external threads 522 of the right half of the drive bolt 520, causing the right deflection rack 530 and left deflection rack 540 to split and translate axially. The right deflection rack 530 can be displaced proximally along an expansion piston 542, as shown in FIG. 20d. The engagement of the teeth 541 of both the right deflection rack 530 and left deflection rack 540 with the pinion 412 can also cause a corresponding distal translation of the left deflection rack. Control members or wires (not shown) connected to one or both of the right and left deflection racks can be tensioned by these translations to deflect the catheter shaft 27.

Figure 20E:
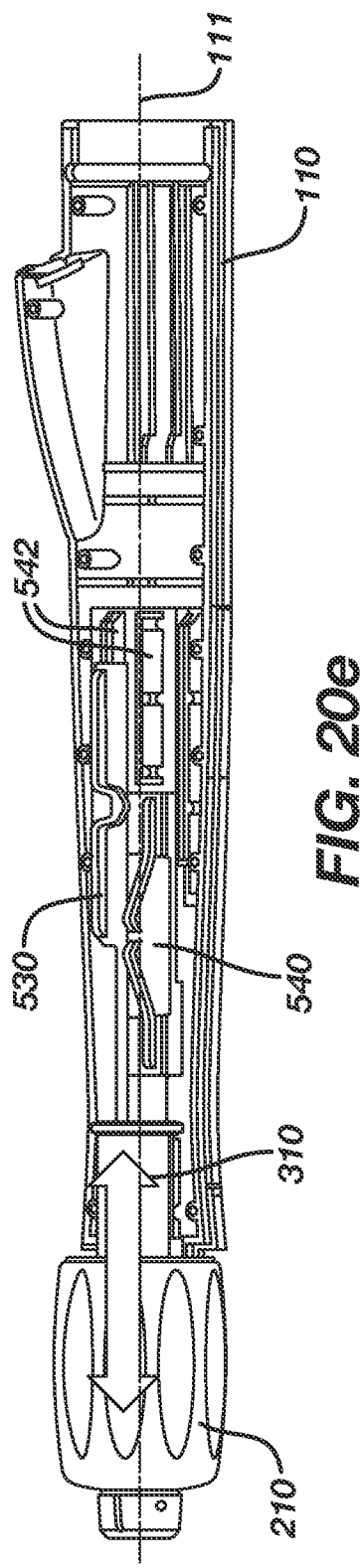

FIG. 20e illustrates that the deflection assumed by the catheter shaft 27 could be maintained, as demonstrated by the continued axial misalignment of the right deflection rack 530 and left deflection rack 540, while the user translates the articulating knob 210 proximally along the longitudinal axis 111. In the reverse of FIG. 20b, the proximal motion of the knob can pull the advancement mechanism 620 and extension collar 630 proximally, increasing the radial size of the balloon (see FIG. 17b) in order to commence or resume the ablation procedure.

Figure 20F:
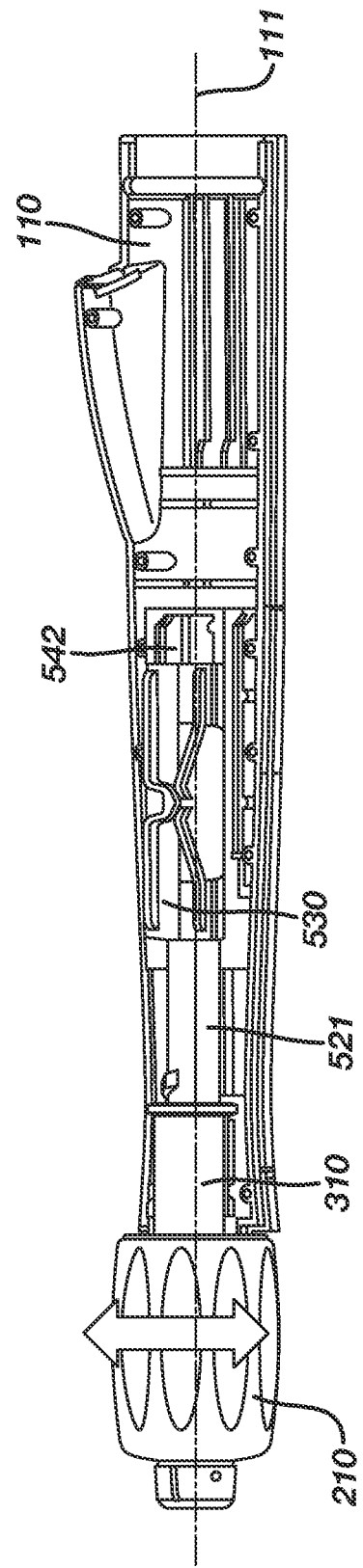

With the articulating knob 210 manipulated back to the original longitudinal starting position, the knob can be rotated in the opposite direction of the rotation applied in FIG. 20c. The rotation of the barrel nut can drive the threads 522 of the right deflection rack 530 to translate distally, rotating the pinion 412 to bring the right deflection rack 530 and left deflection rack 540 of the piston carriage 510 back into longitudinal alignment, as shown in FIG. 20f. The rotation of the knob could also return the catheter shaft 27 to the initial, undeflected state.

As an alternative, linear translation of the articulating knob 210 and the induced motion of the right and left deflation racks 530,540 can be tied to deflections of the catheter tip. In this case, rotation of the articulating knob 210 can be used to change the radial size of the expandable element or balloon or could be used to activate and manipulate various diagnostic capabilities of the catheter.

Figure 21:
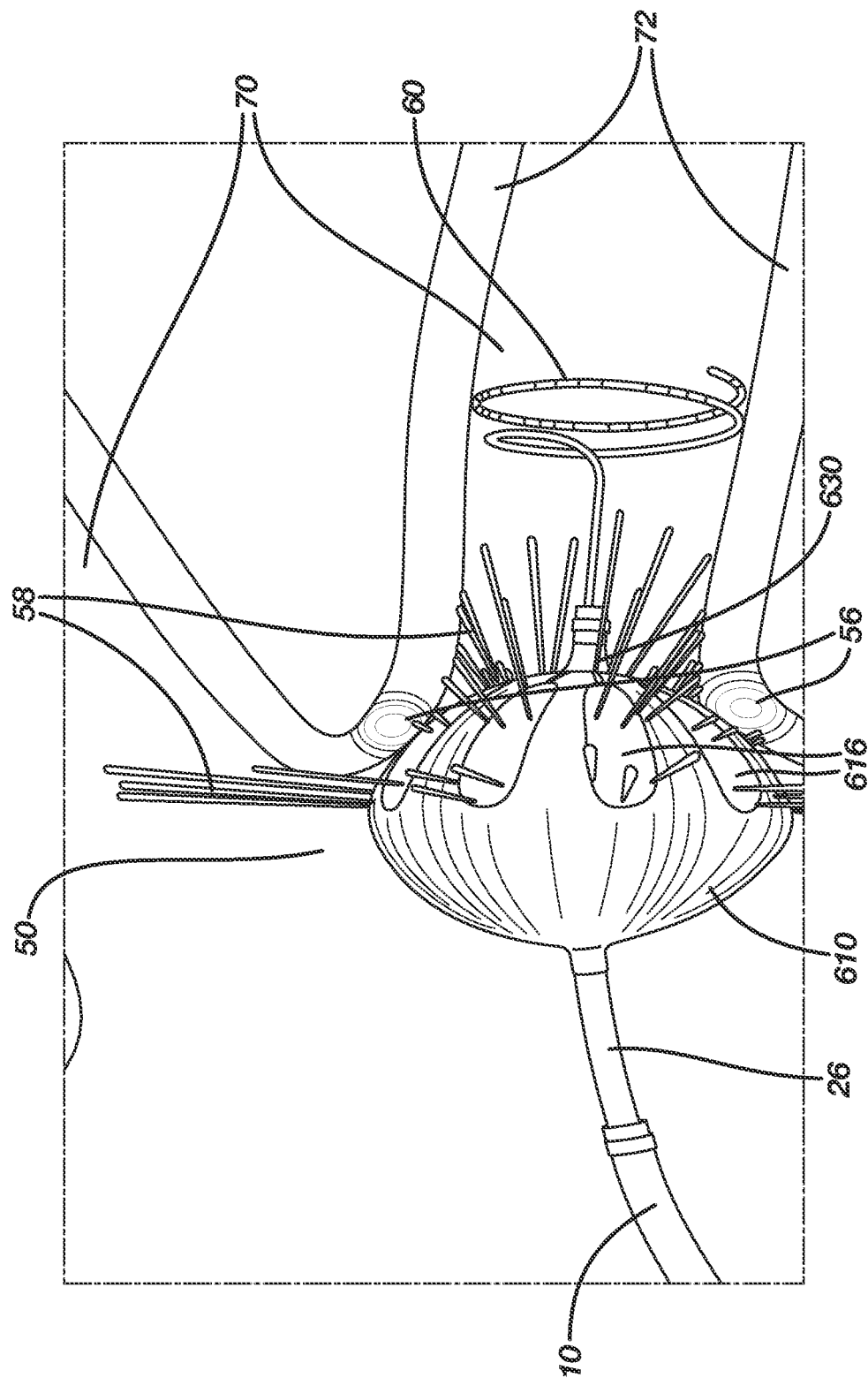
FIG. 21 shows an example of the expandable ablation balloon with independently controlled electrodes around its circumference conducting ablation of the pulmonary veins according to aspects of the present invention.

The multi-electrode balloon 610 of FIG. 6 is shown in FIG. 21 conducting an ablation treatment of a pulmonary vein 70 in the left atrium. The length of the electrodes 616 of the ablation balloon 610 can be chosen to ensure there is contact with the target tissue walls 72 even if the catheter is not perfectly aligned with the ostium of the pulmonary vein 70. The plurality of electrodes 616 can be disposed independent of one another. Functionally, this allows the amount of power delivered to each electrode to be controlled separately to improve safety and the quality of the created lesion in the ablation zone 56. The wire leads from the energy source (not shown) can be shorted to the pads of the electrodes 616, where changes in voltage can be correlated to changes in temperature when the electrode is heated via conductive heat transfer from the ablated tissue.

When deployed from a sheath or outer catheter 10, the balloon 610 can be expanded from its collapsed state to isolate the vein. Similar to the process previously described, the balloon can be expanded by translating the articulating knob 210 proximally to draw the advancement mechanism 620 and the extension collar 630 at the distal end 614 of the balloon towards its proximal end 612, increasing the diameter.

Ablation catheters equipped with multi-function tips are often fitted with small pumps for irrigation. For example, heparinized normal saline from a pump can be delivered through a luer fitting 40 in the handle 100 distally to the electrode pads 616, which often have perforated holes to permit fluidic flow from the interior to the exterior of the balloon 610. The irrigation flow 58 can allow for tip functions like balloon inflation and the cooling of ablation electrodes 616 and the ablation tissue interface in the ablation zones 56. The flow 58 also serve to displace blood from the treatment site to maintain uninterrupted access.

The lumen 622 of the advancement mechanism 620 can also be used for distal irrigation, contrast, or to deploy auxiliary devices. Such devices could include a guidewire or a small-diameter diagnostic catheter 60 as seen in FIG. 21. The diagnostic catheter could be of hypotube construction and deploy from the lumen 622 into a distal hoop shape for stimulation and recording of signals within the atria of the heart.

Figure 22:
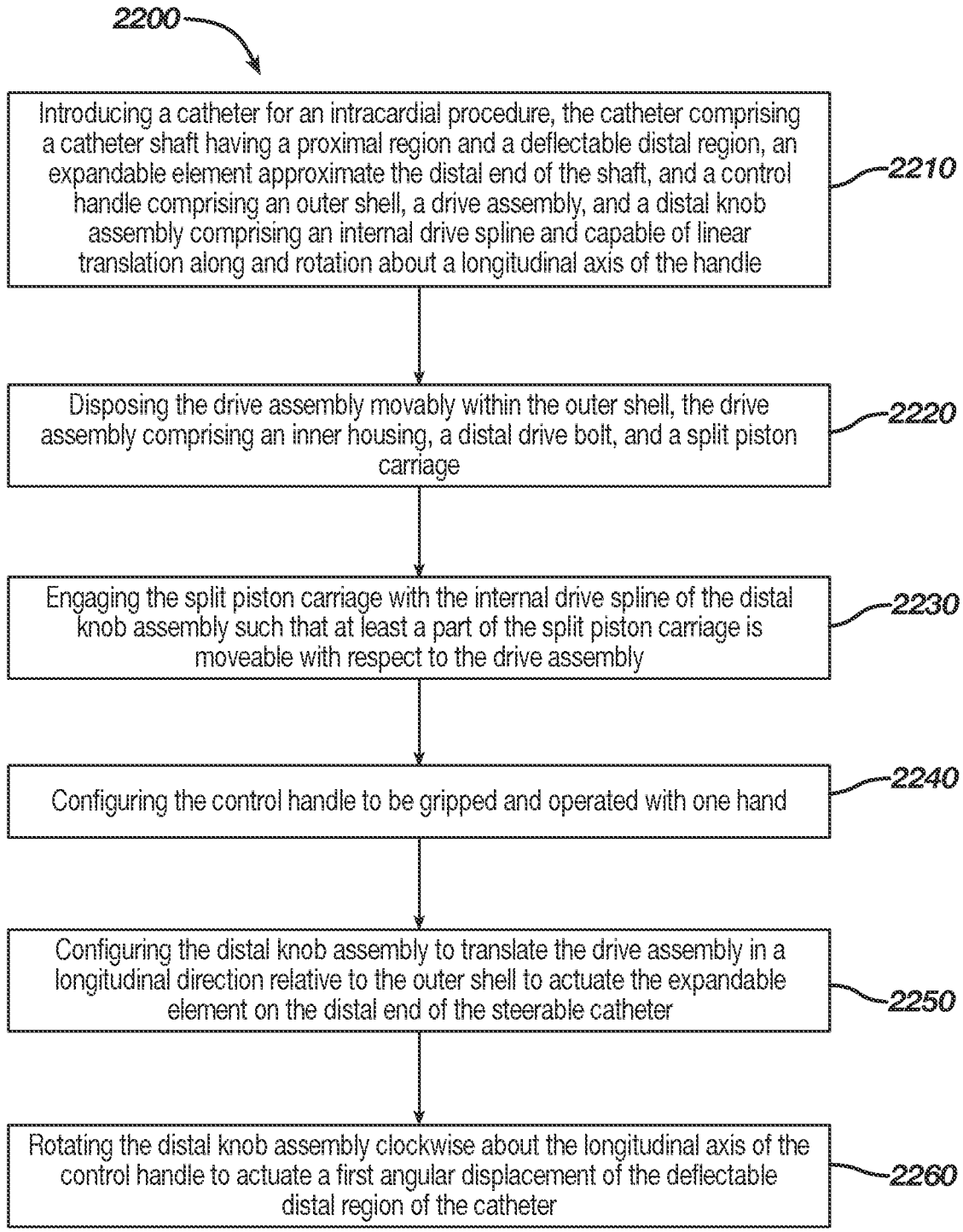
FIGS. 22 and 23 are flow diagrams outlining a method for using the control handle to operate the distal tip of a steerable catheter according to aspects of the present invention.
Figure 23:
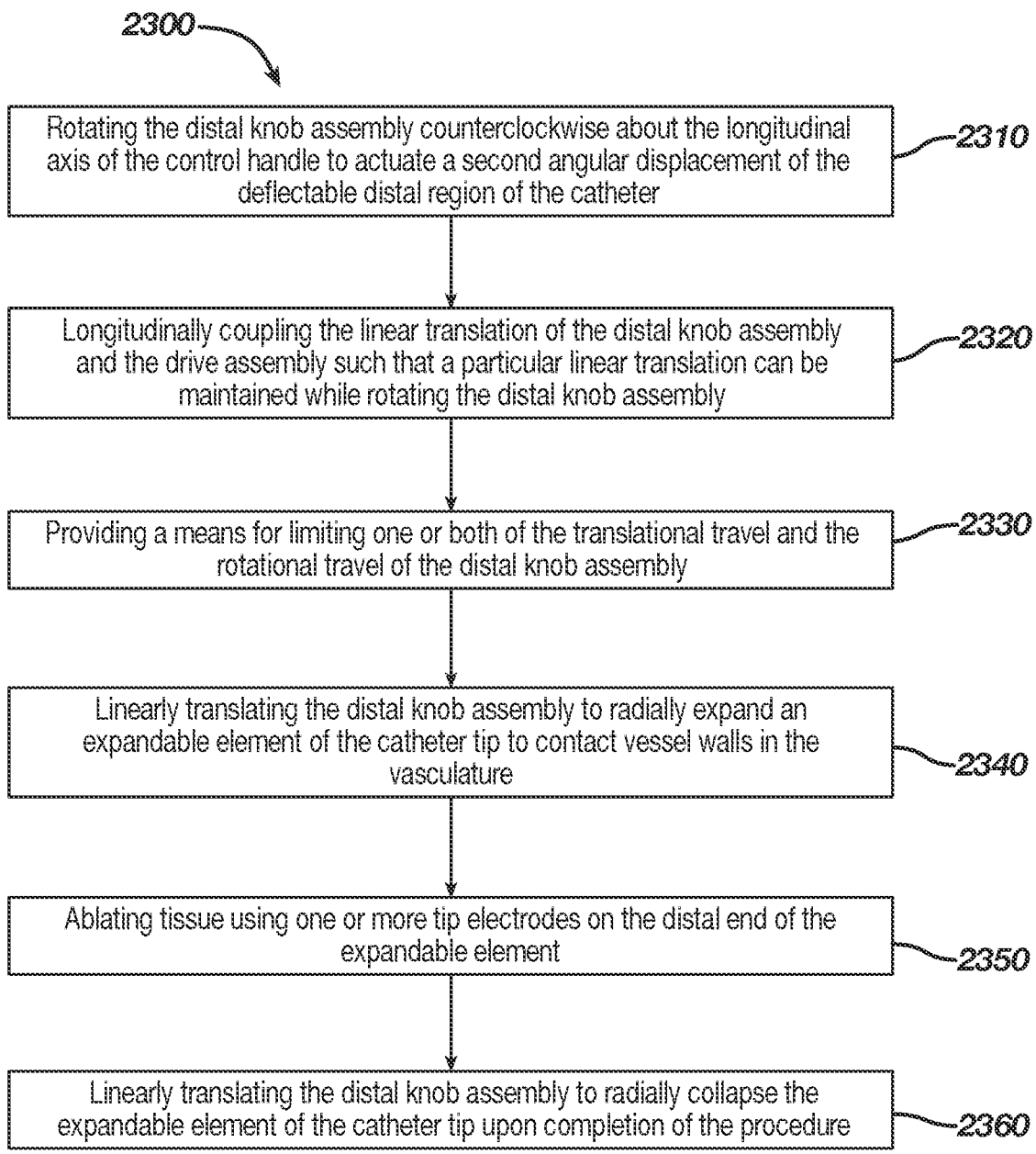

FIG. 22 and FIG. 23 are flow diagrams each comprising method steps for performing a medical procedure using the control handle disclosed herein. The method steps can be implemented by any of the devices and/or apparatus described herein and could be performed in a sequence other than that listed.

Referring to method 2200 outlined in FIG. 22, step 2210 involves introducing a catheter for an intracardial procedure. The catheter can include a catheter shaft having a proximal region and a deflectable distal region, and expandable element or member approximate the distal end of the shaft, and a control handle. The control handle can have an outer shell, a drive assembly, and a distal knob assembly having an internal drive spline and capable of linear translation along and rotation about a longitudinal axis of the handle. Step 2220 involves disposing the drive assembly movably within the outer shell of the control handle so that it can translate along the longitudinal axis of the handle. The drive assembly can have an inner housing, a distal drive bolt with external threads, and a split piston carriage.

In step 2230, the split piston carriage is engaged with helical threads of the internal drive spline of the knob assembly so that at least a part of the split piston carriage is moveable with respect to the drive housing. When engaged, rotation of the knob assembly will result in linear translation of at least a part of the piston carriage within the drive housing. In step 2240, the control handle is configured to be operated with one hand, with the thumb and forefingers able to manipulate all the capable functions of the handle without the need for visual reference.

Manipulation of the distal knob assembly of the control handle can actuate various functions of the steerable tip of the catheter. Step 2250 can involve configuring the distal knob assembly to translate the drive assembly in a longitudinal direction relative to the outer shell. This translation can actuate a change in the radial size of the expandable element at the distal end of the steerable catheter. A distal translation of the drive assembly can decrease the radial size, while a proximal motion of the drive assembly can increase the radial size.

Referring to steps 2260 of FIG. 22 and 2310 of FIG. 23, rotation of the distal knob assembly could angularly deflect the distal region of the catheter. In one example, the deflection could be planar, such that clockwise rotation of the knob deflects the distal region in a first direction and counterclockwise rotation causes a deflection in a second direction opposite the first.

Further in FIG. 23, in step 2320 the linear translation of the drive assembly and the distal knob assembly can be coupled independently of the rotation of the knob assembly. A particular linear translation of the drive assembly and the knob assembly could then be maintained while rotating the knob to deflect and steer the distal region of the catheter. In step 2330, the distal knob assembly of the control handle could have limited overall translational travel and rotational travel. For example, physical stop features could be molded within the outer shell of the handle, or shims placed to limit the total proximal and distal travel available to the drive housing. The length of the externally threaded portion of the deflection racks could be chosen to stop further knob rotation in the clockwise or counterclockwise directions, setting the design limits of catheter tip deflections. Grooves or relief cuts configured to engage the knob assembly at various distances of translational travel so that intermediate radial sizes of the expandable element could be affected. Intermediate sizes could be advantageous by allowing the expandable element to adapt in size to conform with various features or geometries of the target vasculature. Those with skill in the art could appreciate other benefits of setting travel limits or being able to adjust the size of the expandable element of the catheter tip in-situ.

Step 2340 involves linearly translating the distal knob assembly to increase the radial size of the expandable element. This process is can be useful for performing diagnostic, therapeutic, and/or other procedures. For example, and not by way of limitation, a cardiac ablation procedure can involve contacting tissue around the ostium of the pulmonary veins with one or more electrodes of the catheter tip for the transmission of energy. The energy from the one or more electrodes can then be used in step 2350 to ablate tissue and create a lesion of scar tissue in the treatment of PAF or other heart arrhythmia. In other examples, the energy can be used for imagery or mapping procedures.

Upon completion of a procedure, there is often a need to retract deployed devices back into a sheath or outer catheter so they can be safely removed from the patient. In step 2360 the distal knob assembly is linearly translated to decrease the radial size of the expandable element so that it can be withdrawn into the inner diameter of the sheath or outer catheter.

The invention is not necessarily limited to the examples described, which can be varied in construction and detail. The terms "distal" and "proximal" are used throughout the preceding description and are meant to refer to a positions and directions relative to a treating physician. As such, "distal" or distally" refer to a position distant to or a direction away from the physician. Similarly, "proximal" or "proximally" refer to a position near to or a direction towards the physician. Furthermore, the singular forms "a," "an," and "the" include plural referents unless the context clearly dictates otherwise.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 99%.

In describing example embodiments, terminology has been resorted to for the sake of clarity. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Some steps of a method can be performed in a different order than those described herein without departing from the scope of the disclosed technology. Similarly, it is also to be understood that the mention of one or more components in a device or system does not preclude the presence of additional components or intervening components between those components expressly identified. For clarity and conciseness, not all possible combinations have been listed, and such modifications are often apparent to those of skill in the art and are intended to be within the scope of the claims which follow.

What is claimed is:

1. A control handle for a catheter having a steerable tip, the control handle comprising:
    a tubular outer housing defining a longitudinal axis, a proximal end, and a distal end;
    an articulating knob adjacent the distal end of the tubular outer housing, the articulating knob rotatable about and linearly displaceable along the longitudinal axis of the tubular outer housing; and
    a drive housing movably disposed within the tubular outer housing and coupled to the articulating knob, the drive housing comprising a split piston carriage comprising a drive bolt, a right deflection rack, and a left deflection rack, the articulating knob being configured to impart:
        a first linear displacement on the drive housing when the articulating knob is rotated clockwise about the longitudinal axis of the tubular outer housing, the first linear displacement deflecting the steerable tip in a first lateral direction;
        a second linear displacement on the drive housing opposite the first linear displacement when the articulating knob is rotated counterclockwise about the longitudinal axis of the tubular outer housing, the second linear displacement deflecting the steerable tip in a second lateral direction; and
        a third linear displacement on the drive housing configured to change the radial size of an expandable element on the distal end of the catheter when the articulating knob is linearly displaced a distance parallel to the longitudinal axis;
    an advancement mechanism comprising an elongate tubular member mechanically coupled distally to the expandable element via a collar and proximally to the drive housing;

a first control wire attached proximally to the right deflection rack and distally to a first attachment at the steerable tip; and a second control wire attached proximally to the left deflection rack and distally to a second attachment at the steerable tip, wherein the third linear displacement causes the elongate tubular member to translate independently of the first attachment and the second attachment.

2. The control handle of claim 1, wherein a linear translation in the advancement mechanism causes in a change in a radial size of the expandable element.

3. The control handle of claim 1, wherein the expandable element comprises a balloon.

4. The control handle of claim 3, wherein the balloon comprises a plurality of independently controlled electrodes equally spaced around the circumference of the balloon.

5. The control handle of claim 1, wherein the elongate tubular member comprises an internal hollow lumen.

6. The control handle of claim 1, the articulating knob further comprising a hub, a proximal end, a distal opening, and at least one keyway.

7. The control handle of claim 6, further comprising a barrel nut coupled to the articulating knob and rotatable about the longitudinal axis of the tubular outer housing, the barrel nut comprising one or more keys disposed at one end, a thrust collar at the other end, and a drive spline disposed inside the barrel nut.

8. The control handle of claim 7, wherein the barrel nut being longitudinally coupled to the drive housing by the thrust collar, the thrust collar being configured to linearly displace the drive housing when the articulating knob is linearly displaced along the longitudinal axis.

9. The control handle of claim 7, wherein the barrel nut being configured to be rotationally coupled to the articulating knob by the one or more keys.

10. The control handle of claim 7, wherein the drive spline being configured to engage threads of the split piston carriage to displace at least a part of the piston carriage along a linear path when the articulating knob is rotated.

11. The control handle of claim 1, wherein clockwise rotation of the articulating knob results in the linear translation of the right deflection rack relative to the left deflection rack in a first direction.

12. The control handle of claim 11, wherein counterclockwise rotation of the articulating knob results in the linear translation of the right deflection rack relative to the left deflection rack in a second direction opposite the first direction.

13. The control handle of claim 11, further comprising a pinion coupled to the right deflection rack and left deflection rack, the pinion rotating when the right deflection rack translates linearly with respect to the left deflection rack.

14. The control handle of claim 1, the articulating knob being linearly displaceable independent of being rotated about the longitudinal axis.

15. The control handle of claim 1, wherein the elongate tubular member of the advancement mechanism comprises a flexible polyimide tube.

16. The control handle of claim 1, further comprising a luer fitting configured to receive fluid injection.

* * * * *